US008907151B2

(12) United States Patent
Voskoboynikov et al.

(10) Patent No.: US 8,907,151 B2
(45) Date of Patent: Dec. 9, 2014

(54) CONVERSION OF METHANE TO AROMATIC COMPOUNDS USING UZM-39 ALUMINOSILICATE ZEOLITE

(71) Applicant: UOP LLC, Des Plaines, IL (US)

(72) Inventors: Timur V. Voskoboynikov, Arlington Heights, IL (US); Christopher P. Nicholas, Evanston, IL (US); Mark A. Miller, Niles, IL (US); Lisa M. King, Westchester, IL (US); Vincent G. Mezera, Brookfield, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/102,993

(22) Filed: Dec. 11, 2013

(65) Prior Publication Data

US 2014/0163282 A1 Jun. 12, 2014

Related U.S. Application Data

(60) Provisional application No. 61/736,287, filed on Dec. 12, 2012.

(51) Int. Cl.
*C07C 2/76* (2006.01)
*B01J 29/78* (2006.01)

(52) U.S. Cl.
CPC ... *B01J 29/78* (2013.01); *C07C 2/76* (2013.01)
USPC .......................................... 585/418; 585/419

(58) Field of Classification Search
USPC ................................................. 585/418, 419
See application file for complete search history.

(56) References Cited

U.S. PATENT DOCUMENTS

| | | | |
|---|---|---|---|
| 2,620,314 A | 12/1952 | Hoekstra | |
| 2,948,675 A | 8/1960 | Case et al. | |
| 3,146,188 A | 8/1964 | Gossett | |
| 3,227,645 A | 1/1966 | Frumkin et al. | |
| 3,658,695 A | 4/1972 | VanPool | |
| 3,839,187 A | 10/1974 | Vanvenrooy | |
| 4,197,192 A | 4/1980 | Gould | |
| 4,310,440 A | 1/1982 | Wilson et al. | |
| 4,354,928 A | 10/1982 | Audeh et al. | |
| 4,440,871 A | 4/1984 | Lok et al. | |
| 4,478,705 A | 10/1984 | Ganguli | |
| 4,483,691 A | 11/1984 | McShea, III et al. | |
| 4,645,589 A | 2/1987 | Krambeck et al. | |
| 4,870,222 A | 9/1989 | Bakas et al. | |
| 5,157,196 A | 10/1992 | Crossland et al. | |
| 5,157,197 A | 10/1992 | Cooper et al. | |
| 5,961,786 A | 10/1999 | Freel et al. | |
| 6,136,290 A | 10/2000 | Benazzi et al. | |
| 6,239,057 B1 | 5/2001 | Ichikawa et al. | |
| 6,426,442 B1 | 7/2002 | Ichikawa et al. | |
| 6,514,479 B1 | 2/2003 | Merlen et al. | |
| 6,613,302 B1 | 9/2003 | Moscoso et al. | |
| 6,627,781 B1 | 9/2003 | Briot et al. | |
| 6,740,788 B1 | 5/2004 | Maher et al. | |
| 6,756,030 B1 | 6/2004 | Rohde et al. | |
| 6,776,975 B2 | 8/2004 | Wilson et al. | |
| 7,374,662 B2 | 5/2008 | Duplan et al. | |
| 7,419,931 B2 | 9/2008 | Serra et al. | |
| 7,575,737 B1 | 8/2009 | Miller et al. | |
| 7,615,143 B2 | 11/2009 | Chen et al. | |
| 7,629,499 B2 | 12/2009 | Serra Alfaro et al. | |
| 7,638,667 B2 | 12/2009 | Jan et al. | |
| 7,687,423 B2 | 3/2010 | Moscoso et al. | |
| 7,713,513 B2 | 5/2010 | Jan et al. | |
| 7,915,469 B2 | 3/2011 | Miller et al. | |
| 7,982,083 B2 | 7/2011 | Guillon et al. | |
| 8,048,403 B2 | 11/2011 | Miller et al. | |
| 8,058,495 B2 | 11/2011 | Jan et al. | |
| 8,134,037 B2 | 3/2012 | Bogdan et al. | |
| 8,178,740 B2 | 5/2012 | Nicholas et al. | |
| 8,183,172 B2 | 5/2012 | Guillon et al. | |
| 8,263,032 B2 | 9/2012 | Andersen et al. | |
| 8,398,955 B2 | 3/2013 | Lai et al. | |
| 8,461,405 B2 | 6/2013 | Sanchez et al. | |
| 8,609,910 B1 | 12/2013 | Nicholas et al. | |
| 8,609,911 B1 | 12/2013 | Nicholas et al. | |

(Continued)

FOREIGN PATENT DOCUMENTS

| | | |
|---|---|---|
| CA | 2268803 A1 | 4/1998 |
| CN | 102040459 | 5/2011 |

(Continued)

OTHER PUBLICATIONS

Hong et al., "Synthesis, Structure Solution, Characterization, and Catalytic Properties of TNU-10: A High-Silica Zeolite with the STI Topology", J. Am. Chem Society, 2004, vol. 126, pp. 5718-5826.

Gramm et al., "Complex zeolite structure solved by combining powder diffraction and electron microscopy", Nature, 2006, vol. 444, pp. 79-81.

Baerlocher et al., "Structure of Polycrystalline Zeolite Catalyst IM-5 Solved by Enhanced Charge Flipping", Science, 2007, vol. 315, pp. 1113-1116.

(Continued)

*Primary Examiner* — Thuan D Dang
(74) *Attorney, Agent, or Firm* — Maryann Maas

(57) ABSTRACT

A new family of coherently grown composites of TUN and IMF zeotypes has been synthesized and shown to be effective catalysts in processes for converting at least one aliphatic hydrocarbon having from 1 to about 4 carbon atoms in a feedstream to provide at least one aromatic hydrocarbon. These zeolites are represented by the empirical formula.

$$Na_nM_m^{k+}T_rAl_{1-x}E_xSi_yO_z$$

where M represents zinc or a metal or metals from Group 1, Group 2, Group 3 or the lanthanide series of the periodic table, T is the organic structure directing agent or agents and E is a framework element such as gallium. The process involves contacting a low carbon number aliphatic hydrocarbon with the coherently grown composite of TUN and IMF zeotypes to produce at least an aromatic.

17 Claims, 13 Drawing Sheets

(56) References Cited

U.S. PATENT DOCUMENTS

| | | |
|---|---|---|
| 8,609,919 B1 | 12/2013 | Nicholas et al. |
| 8,609,920 B1 | 12/2013 | Miller et al. |
| 8,609,921 B1 | 12/2013 | Nicholas et al. |
| 8,618,343 B1 | 12/2013 | Nicholas et al. |
| 8,623,321 B1 | 1/2014 | Miller et al. |
| 8,633,344 B2 | 1/2014 | Nicholas et al. |
| 8,642,823 B2 | 2/2014 | Nicholas et al. |
| 2008/0179221 A1 | 7/2008 | Nguyen et al. |
| 2010/0144513 A1 | 6/2010 | Nicholas et al. |
| 2010/0144514 A1 | 6/2010 | Nicholas et al. |
| 2010/0298117 A1 | 11/2010 | Levin et al. |
| 2011/0174692 A1 | 7/2011 | Negiz et al. |
| 2011/0178354 A1 | 7/2011 | Negiz et al. |
| 2011/0178356 A1 | 7/2011 | Negiz et al. |
| 2012/0024752 A1 | 2/2012 | Chen et al. |
| 2012/0029256 A1 | 2/2012 | Chen et al. |
| 2012/0121486 A1 | 5/2012 | Collier et al. |

FOREIGN PATENT DOCUMENTS

| | | |
|---|---|---|
| DE | 69710612 | 11/2002 |
| GB | 682387 | 11/1952 |
| GB | 915601 | 1/1963 |
| JP | 11253810 | 9/1999 |
| JP | 4595106 | 12/2010 |
| KR | 480229 | 3/2005 |
| KR | 2011047178 | 5/2011 |
| KR | 2012023156 | 3/2012 |
| KR | 1174099 | 8/2012 |
| KR | 2012091865 | 8/2012 |
| WO | 9817581 | 4/1998 |
| WO | 2012027034 A2 | 3/2012 |

OTHER PUBLICATIONS

Rietveld, "A Profile Refinement Method for Nuclear and Magnetic Structures", Journal of Applied Crystallography, 1969, vol. 2, pp. 65-71.

Brunauer et al., "Adsorption of Gases in Multimolecular Layers", J. Am. Chem Society, 1938, vol. 60, pp. 309-319.

Portilla et al., "Structure-reactivity relationship for aromatics transalkylation and isomerization process with TNU-9, MCM-22 and ZSM-5 zeolites, and their industrial implications", Applied Catalysis A: General, 2011, vol. 393, n 1-2, pp. 257-268.

Serra et al., "A rational design of alkyl-aromatics dealkylation-transalkylation catalysts using C8 and C9 alkyl-aromatics as reactants", Journal of Catalysis, 2004, vol. 227, n 2, pp. 459-469.

Cejka et al., "Novel zeolites in transformation of aromatic hydrocarbons", King Fahd University of Petroleum and Minerals—18th Annual Saudi-Japan Symposium on Catalysts in Petroleum Refining and Petrochemicals, Nov. 2008, pp. 117-126, Publisher: King Fahd Univ. of Petroleum and Minerals Res. Inst.

Bleken et al., "Conversion of methanol over 10-ring zeolites with differing volumes at channel intersections: Comparison of TNU-9, IM-5, ZSM-11 and ZSM-5w", Physical Chemistry Chemical Physics, 2011, vol. 13, n 7, pp. 2539-2549.

Odedairo et al., "Toluene disproportionation and methylation over zeolites TNU-9, SSZ-33, ZSM-5, and mordenite using different reactor systems", Industrial and Engineering Chemistry Research, 2011, vol. 50, n 6, pp. 3169-3183.

Corma et al., "IM-5: A highly thermal and hydrothermal shape-selective cracking zeolite", Journal of Catalysis, 2002, vol. 206, n 1, pp. 125-133.

Jae et al., "Production of green aromatics from catalytic fast pyrolysis of lignocellulosic biomass", 11AlChE—2011 AlChE Annual Meeting, Conference Proceedings, Oct. 16-21, 2011, Publisher: American Institute of Chemical Engineers.

Jae et al., "Investigation into the shape selectivity of zeolite catalysts for biomass conversion", Journal of Catalysis, 2011, vol. 279, n 2, pp. 257-268.

Tukur et al., "Comparison studies of xylene isomerization and disproportionation reactions between SSZ-33, TNU-9, mordenite and ZSM-5 zeolite catalysts", Chemical Engineering Journal, vol. 166, n 1, pp. 348-357, Jan. 1, 2011.

Hong et al., "Synthesis, crystal structure, characterization, and catalytic properties of TNU-9", Journal of the American Chemical Society, 2007, vol. 129, n 35, pp. 10870-10885.

Corma et al., "Determination of the pore topology of zeolite IM-5 by means of catalytic test reactions and hydrocarbon adsorption measurements", Journal of Catalysis, 2000, vol. 189, n 2, pp. 382-394.

Lee et al., "Synthesis, characterization, and catalytic properties of zeolites IM-5 and NU-88", Journal of Catalysis, 2003, vol. 215, n. 1, pp. 151-170.

Palomares et al., "Co-exchanged IM5, a stable zeolite for the selective catalytic reduction of NO in the presence of water and SO2", Industrial and Engineering Chemistry Research, 2003, vol. 42, n 8, pp. 1538-1542.

He et al., "A theoretical study of the stability of Cu2+ ion in IM-5 zeolite and the interaction of Cu-IM-5 with NO", Microporous and Mesoporous Materials, 2009, vol. 121, n 1-3, pp. 95-102.

Liu et al., "Synthesis of Mo/TNU-9 (TNU-9 Taejon National University No. 9) catalyst and its catalytic performance in methane non-oxidative aromatization", Energy, 2011, vol. 36, n 3, pp. 1582-1589.

Liu et al., "Synthesis of Mo/IM-5 catalyst and its catalytic behavior in methane non-oxidative aromatization", Fuel, 2011, vol. 90, n 4, pp. 1515-1521.

Li et al., "Deep oxidative desulfurization of fuels in redox ionic liquids based on iron chloride", Green Chemistry, 2009, vol. 11, pp. 810-815.

Feng et al., "Application of phosphate ionic liquids in deep desulfurization of fuel", Petrochemical Technology, 2006, vol. 35, pp. 272-276.

Nie et al., "N, N-dialkylimidazolium dialkylphosphate ionic liquids: Their extractive performance for thiopene series compounds from fuel oils versus the length of alkyl group", Fuel Processing Technology, 2008, vol. 89, pp. 978-983.

U.S. Appl. No. 13/714,486, filed Dec. 14, 2012, Nicholas et al.
U.S. Appl. No. 13/714,539, filed Dec. 14, 2012, Nicholas et al.
U.S. Appl. No. 13/714,504, filed Dec. 14, 2012, Nicholas et al.
U.S. Appl. No. 14/102,524, filed Dec. 11, 2013, Voskoboynikov et al.
U.S. Appl. No. 14/102,849, filed Dec. 11, 2013, Voskoboynikov et al.
U.S. Appl. No. 14/102,523, filed Dec. 11, 2013, Nicholas et al.
U.S. Appl. No. 14/094,060, filed Dec. 2, 2013, Nicholas et al.

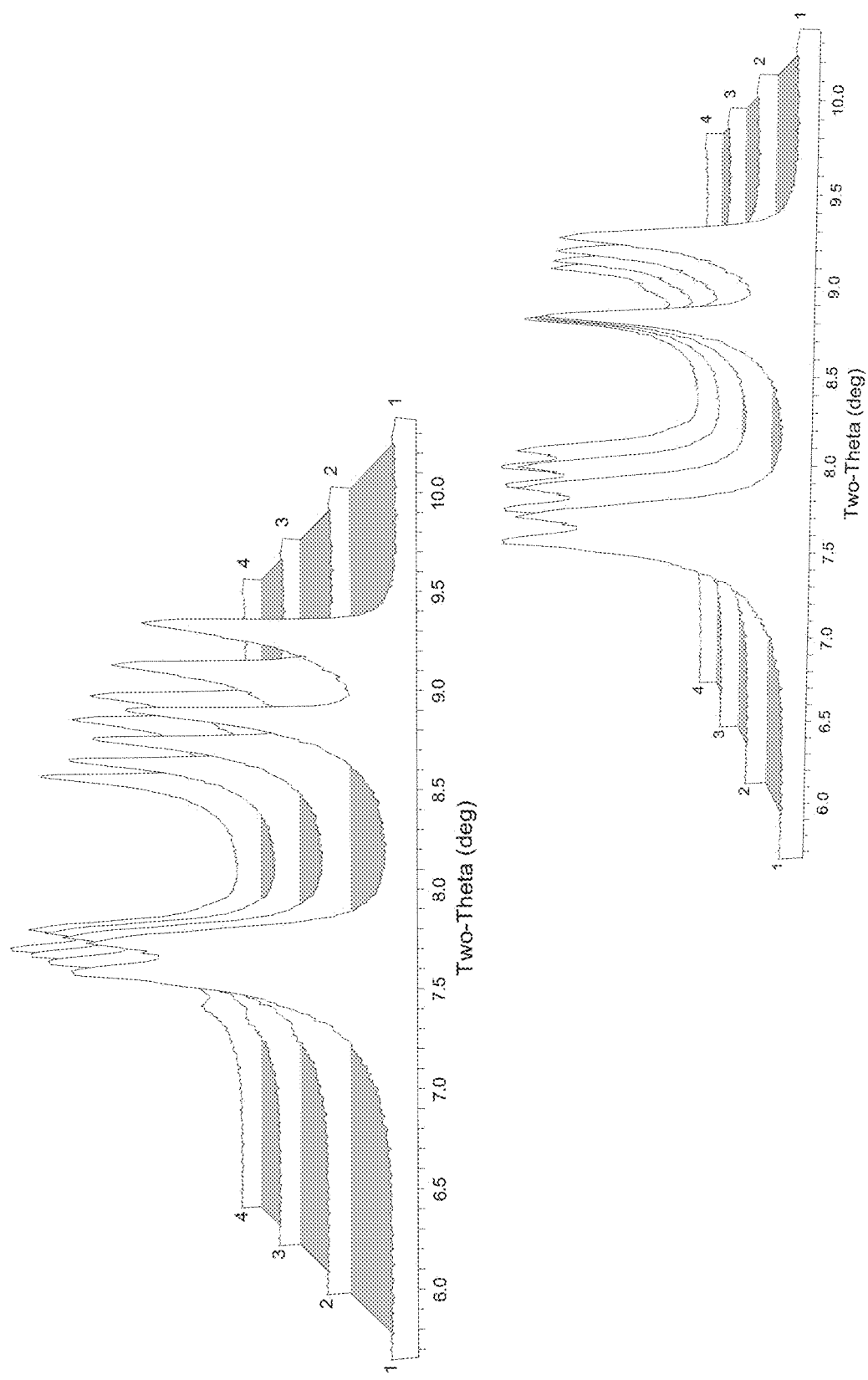

CONVERSION OF METHANE TO AROMATIC COMPOUNDS USING UZM-39 ALUMINOSILICATE ZEOLITE

CROSS-REFERENCE TO RELATED APPLICATIONS

This application claims priority from Provisional Application No. 61/736,287 filed on Dec. 12, 2012, the contents of which are hereby incorporated by reference in its entirety.

FIELD OF THE INVENTION

This invention relates to using a new family of aluminosilicate zeolites designated UZM-39 as the catalytic composite for the conversion of at least one low carbon number aliphatic hydrocarbon, such as methane, to at least one aromatic compound, such as benzene. The zeolite family is represented by the empirical formula of:

$$Na_n M_m^{k+} T_r Al_{1-x} E_x Si_y O_z$$

where M represents a metal or metals from zinc or Group 1 (IUPAC 1), Group 2 (IUPAC 2), Group 3 (IUPAC 3) or the lanthanide series of the periodic table, T is the organic directing agent derived from reactants R and Q where R is an A,Ω-dihalosubstituted alkane such as 1,4-dibromobutane and Q is at least one neutral amine having 6 or fewer carbon atoms such as 1-methylpyrrolidine. E is a framework element such as gallium. The zeolite may further comprise a promoter such as molybdenum or tungsten.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolite, designated TNU-9, was first disclosed by Hong et al. in 2004, (J. Am. Chem. Soc. 2004, 126, 5817-26) and then in a Korean Patent granted in 2005, KR 480229. This report and patent was followed by a full report of the synthesis in 2007 (J. Am. Chem. Soc. 2007, 129, 10870-85). These papers describe the synthesis of TNU-9 from the flexible dicationic structure directing agent, 1,4-bis(N-methylpyrrolidinium)butane dibromide in the presence of sodium. After the structure of TNU-9 was solved (Nature, 2006, 444, 79-81), the International Zeolite Association Structure Commission gave the code of TUN to this zeolite structure type, see Atlas of Zeolite Framework Types, which is maintained by the International Zeolite Association Structure Commission at http://www.iza-structure.org/databases/. The TUN structure type was found to contain 3 mutually orthogonal sets of channels in which each channel is defined by a 10-membered ring of tetrahedrally coordinated atoms. In addition, 2 different sizes of 10-membered ring channels exist in the structure.

Another particular zeolite, IM-5 was first disclosed by Benazzi, et al. in 1996 (FR96/12873; WO98/17581) who describe the synthesis of IM-5 from the flexible dicationic structure directing agent, 1,5-bis(N-methylpyrrolidinium) pentane dibromide or 1,6-bis(N-methylpyrrolidinium)hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was also found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants have successfully prepared a new family of materials designated UZM-39. The topology of the materials is similar to that observed for TNU-9 and IM-5. The materials are prepared via the use of a mixture of simple commercially available structure directing agents, such as 1,4-dibromobutane and 1-methylpyrrolidine, in concert with $Na^+$ using the Layered Material Conversion approach to zeolite synthesis (described below). These materials, designated UZM-39, may be employed as a catalyst in processes for the conversion of low carbon number compounds, such as methane, to at least one aromatic compound, such as benzene.

Literature has proposed to produce aromatic compounds such as benzene, toluene and xylenes from petroleum naphtha streams. Attempts have also been made to produce useful aromatic compounds from low molecular weight aliphatic compounds by, for example, the pyrolysis of natural gas, acetylene and other gases. However, this technique produces benzene and other useful aromatic compounds in very low yields while producing large amounts of tar, insoluble carbon residue and high molecular weight aromatic compounds, all of which are of little commercial use. Specifically, in the pyrolysis of methane and acetylene, the reaction is carried out at a temperature of about 1,000° C. or higher with a conversion rate of only a few percent and a selectivity to naphthalenes of less than 1%, and thus has little practical application.

There are reports in the art of processes for converting natural gas into aromatic compounds. For example, U.S. Pat. No. 5,288,935 discloses a process for producing liquid hydrocarbons from natural gas, in which natural gas is first separated into a methane rich fraction and a $C_2+$ fraction, the methane is then selectively oxidized with oxygen, the effluent from the selective oxidation is then mixed with a part of the $C_2+$ fraction and the resulting mixture pyrolyzed to obtain an aromatic product. The final step is carried out at a temperature of about 300° C. to about 750° C. in the presence of an aromatizing catalyst consisting essentially of a zeolite, gallium, at least one metal from the Group VIII metals and rhenium and at least one additional metal selected from the group consisting of: tin, germanium, lead, indium, thallium, copper, gold, nickel, iron, chromium, molybdenum and tungsten; an alkaline metal or alkaline earth metal and an aluminum matrix.

It is also known that the non-oxidative conversion of methane to benzene via dehydroaromatization can be carried out using Mo/HZSM-5, see L. Wang, L. Tao, M. Xie, G. Xu, J.

Huang, and Y. Yu *Catal. Lett.* 1993, 21, 35 and that dehydrocondensation of methane, optionally in the presence of CO or $CO_2$, to form benzene and naphthalene can be carried out using a molybdenum/HZSM-5 or iron/cobalt modified Mo/HZSM-5, see S. Liu, Q. Dong, R. Ohonishi and M. Ichikawa, *Chem. Commun.* (1998), p. 1217-1218, and S. Liu, L. Wang, Q. Dong, R. Ohonishi, and M. Ichikawa, *Stud. Surf. Sci. Catal.*, Vol. 119, p. 241-246. These catalysts are known to deactivate both by coking and by damage from the repetitive regenerations required in the process. In contrast to this art, a catalyst which comprises a UZM-39 zeolite and which optionally can contain a promoter such as iron, cobalt, tungsten, or molybdenum can be used to successfully catalyze the conversion of at least one low carbon number aliphatic hydrocarbon to at least one aromatic compound. In addition, less deactivation under process conditions may be observed than typical with MFI based catalysts.

SUMMARY OF THE INVENTION

As stated, the present invention relates to using a novel catalytic composite comprising coherently grown composite of TUN and IMF zeotypes designated UZM-39 as the catalytic composite in processes for converting at least one low carbon number aliphatic hydrocarbon having from 1 to about 4 carbon atoms in a feedstream to provide at least one aromatic hydrocarbon. The microporous crystalline zeolite has a three-dimensional framework of at least $AlO_2$ and $SiO_2$ tetrahedral units and an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having from 3 to 6 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k\cdot m+3+4\cdot y)/2$$

and is characterized in that it has TUN regions and IMF regions that are coherently aligned so that the $[010]_{TUN}$ zone axis and the $[001]_{IMF}$ zone axis are parallel to each other and there is continuity of crystal planes of type $(002)_{TUN}$ and $(060)_{IMF}$, where the indexing is referred to monoclinic $C_{2/m}$ and orthorhombic $C_{mcm}$ unit cells for TUN and IMF respectively.

The microporous crystalline zeolite may also be described as having a three-dimensional framework of at least $AlO_2$ and $SiO_2$ tetrahedral units and an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents a metal or metals from Group 1 (IUPAC 1), Group 2 (IUPAC 2), Group 3 (IUPAC 3), the lanthanide series of the periodic table or zinc, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having between 3 and 6 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k\cdot m+3+4\cdot y)/2$$

and the zeolite is characterized in that it has the x-ray diffraction pattern having at least the d-spacings and intensities set forth in Table A1

TABLE A1

| 2θ | d (Å) | I/Io % |
|---|---|---|
| 7.17-7.21 | 12.25-12.31 | vw-m |
| 7.5-8.1* | 11.78-10.91 | w-m |
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections

The zeolite is thermally stable up to a temperature of greater than 600° C. in one embodiment and at least 800° C. in another embodiment.

The Layered Material Conversion approach may be used for preparing the crystalline microporous zeolite described above. The process comprises forming a reaction mixture containing reactive sources of Na, R, Q, Al, Si, seeds of a layered material L and optionally E and/or M and heating the reaction mixture at a temperature of about 150° C. to about 200° C., about 155° C. to about 190° C., or about 160° C. to about 180° C., for a time sufficient to form the zeolite. L does not have the same zeotype as the UZM-39 coherently grown composite. The reaction mixture has a composition expressed in terms of mole ratios of the oxides of:

$$a\text{-}bNa_2O\text{:}bM_{n/2}O\text{:}cRO\text{:}dQ\text{:}1\text{-}eAl_2O_3\text{:}eE_2O_3\text{:}fSiO_2\text{:}gH_2O$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. Additionally, the reaction mixture comprises from about 1 to about 10 wt.-% of seed zeolite L based on the amount of $SiO_2$ in the reaction mixture, e.g., if there is 100 g of $SiO_2$ in the reaction mixture, from about 1 to about 10 g of seed zeolite L would be added to the reaction mixture. With this number of reactive reagent sources, many orders of addition can be envisioned. Typically, the aluminum reagent is dissolved in the sodium hydroxide prior to adding the silica reagents. As can be seen in the examples, reagents R and Q can be added together or separately in many different orders of addition.

The invention uses UZM-39 as the catalyst or a catalyst component in a process for the conversion of low carbon number aliphatic hydrocarbons to higher carbon number hydrocarbons. In one embodiment the UZM-39 catalyst composite may additionally comprise a promoter metal selected from the group consisting of iron, cobalt, vanadium, gallium, zinc, chromium, manganese, molybdenum, tungsten and combinations thereof. The process involves converting low carbon number aliphatic hydrocarbons to higher carbon number hydrocarbons by contacting the low carbon number aliphatic hydrocarbons with a catalyst composite comprising UZM-39 at conditions to give the higher carbon number hydrocarbons.

BRIEF DESCRIPTION OF THE DRAWINGS

FIG. 13 is a plot of the low angle region in XRD analysis of materials showing that small percentages of TUN can be determined in samples largely consisting of IMF.

DETAILED DESCRIPTION OF THE INVENTION

Figure 1:
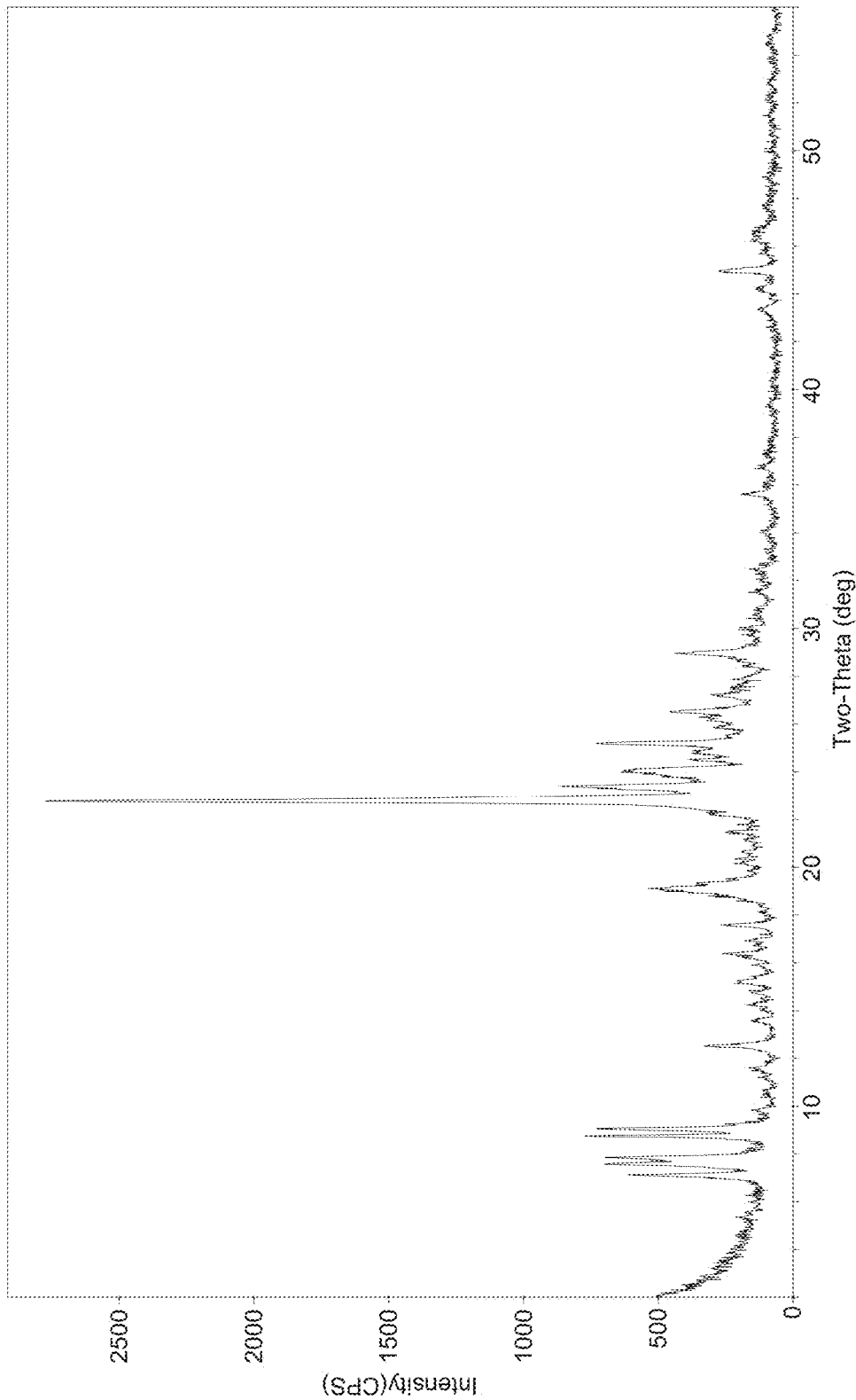
FIG. 1 is an XRD pattern of the UZM-39 zeolite formed in Example 1. This pattern shows the UZM-39 zeolite in the as-synthesized form.

Applicants have prepared a catalytic component suitable for catalyzing the conversion of low carbon number aliphatic hydrocarbons to generate higher carbon number hydrocarbons where the catalytic component comprises an aluminosilicate zeolite whose topological structure is related to TUN as described in Atlas of Zeolite Framework Types, which is maintained by the International Zeolite Association Structure Commission at http://www.iza-structure.org/databases/, the member of which has been designated TNU-9. As will be shown in detail, UZM-39 is different from TNU-9 in a number of its characteristics including its x-ray diffraction pattern (XRD). UZM-39 is also related to IMF as described in the Atlas of Zeolite Framework Types, the member of which has been designated IM-5. As will be shown in detail, UZM-39 is different from TNU-9 and IM-5 in a number of its characteristics including its x-ray diffraction pattern. The instant microporous crystalline zeolite (UZM-39) has an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having between 3 and 6 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

Where M is only one metal, then the weighted average valence is the valence of that one metal, i.e. +1 or +2. However, when more than one M metal is present, the total amount of:

$$M_m^{k+}=M_{m1}^{(k1)+}+M_{m2}^{(k2)+}+M_{m3}^{(k3)+}+M_{m4}^{(k4)+}+\ldots$$

and the weighted average valence "k" is given by the equation:

$$k = \frac{m1 \cdot k1 + m2 \cdot k2 + m3 \cdot k3 \ldots}{m1 + m2 + m3 \ldots}$$

In one embodiment, the microporous crystalline zeolite, UZM-39, is synthesized by a hydrothermal crystallization of a reaction mixture prepared by combining reactive sources of sodium, organic structure directing agent or agents T, aluminum, silicon, seeds of a layered material L, and optionally E, M, or both. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium aluminate, sodium bromide, and sodium silicate.

T is the organic structure directing agent or agents derived from reactants R and Q where R is an A,Ω-dihalogen substituted alkane having between 3 and 6 carbon atoms and Q comprises at least one neutral monoamine having 6 or fewer carbon atoms. R may be an A,Ω-dihalogen substituted alkane having between 3 and 6 carbon atoms selected from the group consisting of 1,3-dichloropropane, 1,4-dichlorobutane, 1,5-dichloropentane, 1,6-dichlorohexane, 1,3-dibromopropane, 1,4-dibromobutane, 1,5-dibromopentane, 1,6-dibromohexane, 1,3-diiodopropane, 1,4-diiodobutane, 1,5-diiodopentane, 1,6-diiodohexane and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine. Q may comprise combinations of multiple neutral monoamines having 6 or fewer carbon atoms.

L comprises at least one seed of a layered zeolite. Suitable seed zeolites are layered materials that are microporous zeolites with crystal thickness in at least one dimension of less than about 30 to about 50 nm. The microporous materials have pore diameters of less than about 2 nm. The seed layered zeolite is of a different zeotype than the UZM-39 coherently grown composite being synthesized. Examples of suitable layered materials include but are not limited to UZM-4M (U.S. Pat. No. 6,776,975), UZM-5 (U.S. Pat. No. 6,613,302), UZM-8 (U.S. Pat. No. 6,756,030), UZM-8HS (U.S. Pat. No. 7,713,513), UZM-26 (US-2010-0152023-A1), UZM-27 (U.S. Pat. No. 7,575,737), BPH, FAU/EMT materials, *BEA or zeolite Beta, members of the MWW family such as MCM-22P and MCM-22, MCM-36, MCM-49, MCM-56, ITQ-1, ITQ-2, ITQ-30, ERB-1, EMM-10P and EMM-10, SSZ-25, and SSZ-70 as well as smaller microporous materials such as PREFER (pre ferrierite), NU-6 and the like.

M represents at least one exchangeable cation of a metal or metals from Group 1 (IUPAC 1), Group 2 (IUPAC 2), Group 3 (IUPAC 3), or the lanthanide series of the periodic table and or zinc. Specific examples of M include but are not limited to lithium, potassium, rubidium, cesium, magnesium, calcium, strontium, barium, zinc, yttrium, lanthanum, gadolinium, and combinations thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium sulfate, gallium nitrate, ferric sulfate, ferric nitrate, ferric chloride and combinations thereof.

The reaction mixture containing reactive sources of the desired components can be described in terms of molar ratios of the oxides by the formula:

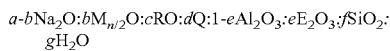

$$a\text{-}b\text{Na}_2\text{O}{:}b\text{M}_{n/2}\text{O}{:}c\text{RO}{:}d\text{Q}{:}1\text{-}e\text{Al}_2\text{O}_3{:}e\text{E}_2\text{O}_3{:}f\text{SiO}_2{:}g\text{H}_2\text{O}$$

where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000. Additionally in the reaction mixture is from about 1 to about 10 wt.-% of seed zeolite L based on the amount of $SiO_2$ in the reaction, e.g., if there is 100 g of $SiO_2$ in the reaction mixture, from about 1 to about 10 g of seed zeolite L would be added. The examples demonstrate a number of specific orders of addition for the reaction mixture which lead to UZM-39. However, as there are at least 6 starting materials, many orders of addition are possible. For example, the seed crystals L can be added as the last ingredient to the reaction mixture, to the reactive Si source, or at other suitable points. Also, if alkoxides are used, a distillation or evaporative step may be included to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 150° C. to about 200° C., about 155° C. to about 190° C., or about 160° C. to about 180° C., for a period of about 1 day to about 3 weeks, and in another embodiment for a time of about 3 days to about 12 days, in a stirred, sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The as-synthesized coherently grown composite of TUN and IMF zeotypes, UZM-39, is characterized by the x-ray diffraction pattern, having at least the d-spacings and relative intensities set forth in Tables A1-A3 below. Diffraction patterns herein were obtained using a typical laboratory powder diffractometer, utilizing the $K_\alpha$ line of copper; Cu K alpha. From the position of the diffraction peaks represented by the angle 2 theta, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case.

Figure 3:
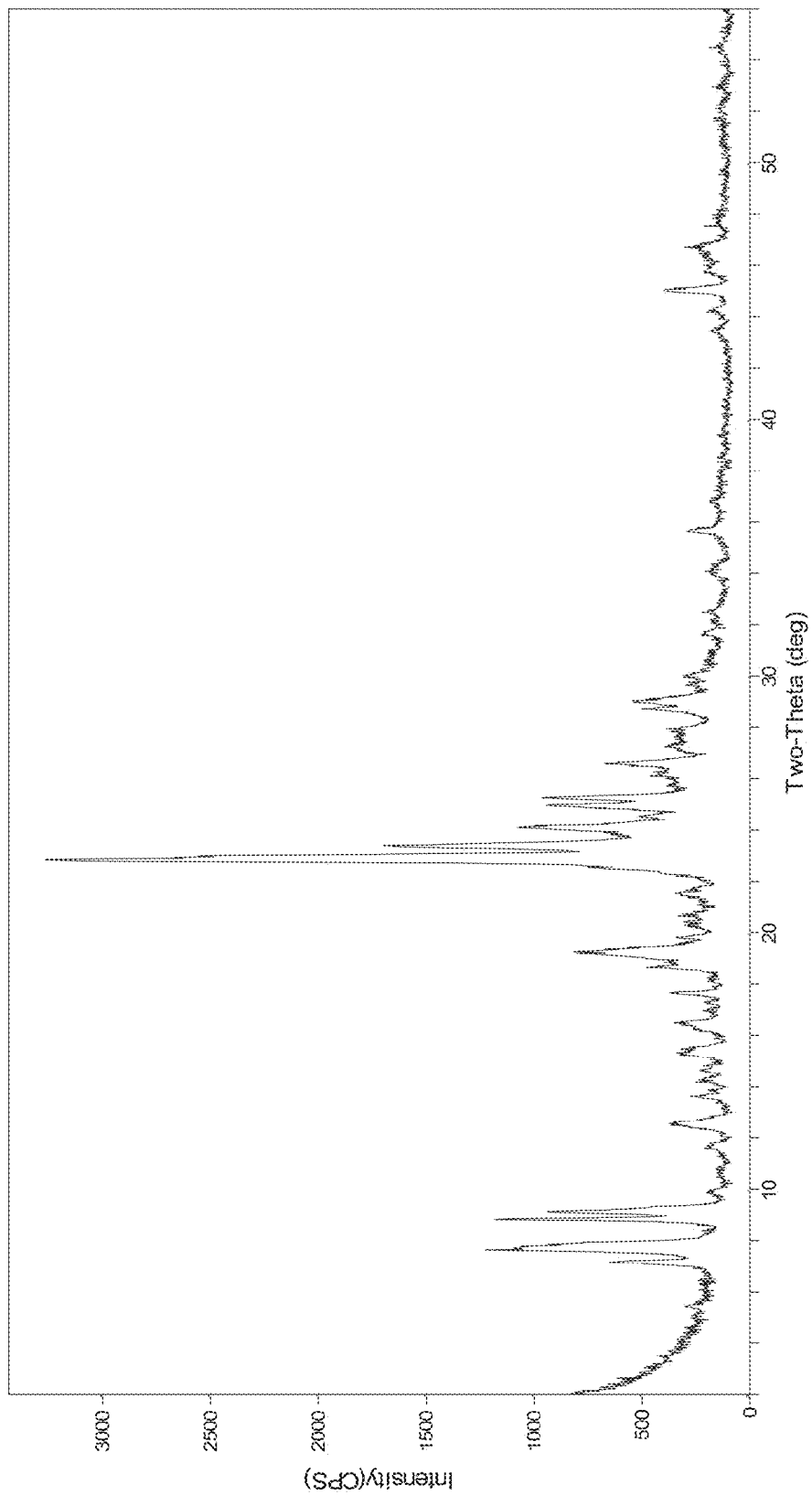
FIG. 3 is an XRD pattern of the UZM-39 zeolite formed in Example 16. This pattern shows the UZM-39 zeolite in the as-synthesized form.
Figure 5:
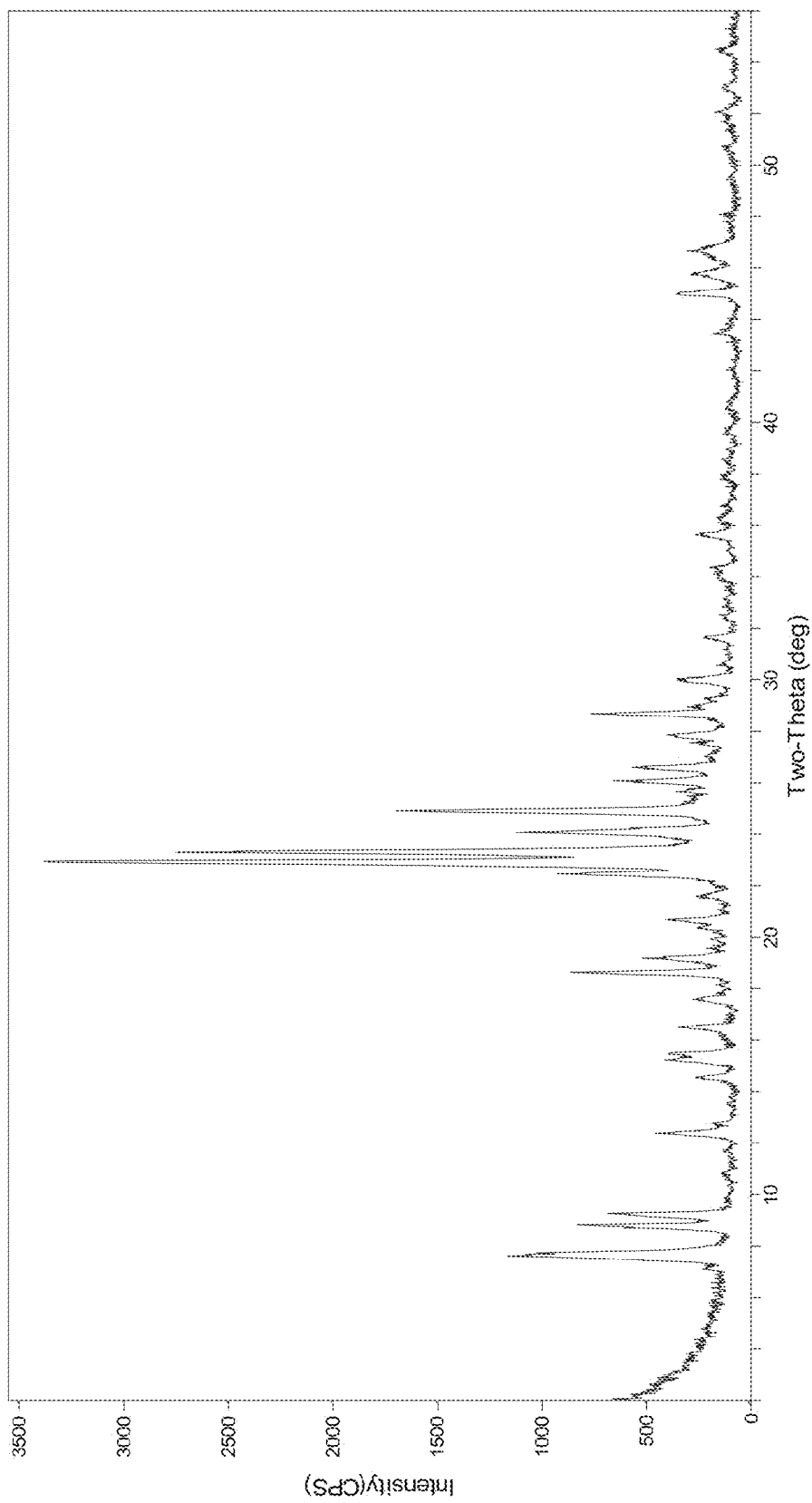
FIG. 5 is an XRD pattern of the UZM-39 zeolite formed in Example 28. This pattern shows the UZM-39 zeolite in the as-synthesized form.

The X-ray diffraction pattern for UZM-39 contains many peaks. Examples of the x-ray diffraction patterns for various as-synthesized UZM-39 products are shown in FIGS. 1, 3, and 5. Those peaks characteristic of UZM-39 are shown in Tables A1-A3 for various coherently grown composite structures. Additional peaks, particularly those of very weak intensity, may also be present. All peaks of medium or higher intensity present in the UZM-39 family of coherently grown composite structures are represented in at least Table A3.

Table A1 contains selected d-spacings and relative intensities of the UZM-39 X-ray diffraction pattern. The relative intensities are shown as a range covering UZM-39 materials with varying relative amounts of TUN and IMF zeotypes.

TABLE A1

| 2θ | d (Å) | I/Io % |
|---|---|---|
| 7.17-7.21 | 12.25-12.31 | vw-m |
| 7.5-8.1* | 11.78-10.91 | w-m |

TABLE A1-continued

| 2θ | d (Å) | I/Io % |
|---|---|---|
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections

The zeolite may be further characterized by the x-ray diffraction pattern having at least the d-spacings and intensities set forth in Table A2 where the d-spacings and intensities are provided at different relative concentrations of the components of the coherently grown composite structure.

TABLE A2

| I high TUN, low IMF | | | II med TUN, med IMF | | | III low TUN, high IMF | | |
|---|---|---|---|---|---|---|---|---|
| 2-Theta | d(f) | I/Io % | 2-Theta | d(f) | I/Io % | 2-Theta | d(f) | I/Io % |
| 7.21 | 12.25 | w-m | 7.17 | 12.31 | w-m | 7.21 | 12.25 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 12.62 | 7.00 | w | 12.50 | 7.08 | w-m | 12.47 | 7.09 | w-m |
| 17.70 | 5.01 | vw-w | 17.72 | 5.00 | w-m | 17.70 | 5.01 | vw-w |
| 19.20 | 4.62 | w-m | 22.8-23.2* | 3.90-3.83 | vs | 18.71 | 4.74 | w-m |
| 22.89 | 3.88 | vs | 23.43 | 3.79 | s | 22.55 | 3.94 | m |
| 23.49 | 3.78 | m | 25.12 | 3.54 | m | 23.03 | 3.86 | vs |
| 25.31 | 3.52 | m | 28.74-29.25* | 3.10-3.05 | w-m | 23.39 | 3.80 | s |
| 29.10 | 3.07 | w | 45.29 | 2.00 | w | 25.01 | 3.56 | m |
| 45.08 | 2.01 | w | | | | 28.76 | 3.10 | w-m |
| | | | | | | 45.08 | 2.01 | w |

*composite peak consisting of multiple overlapping reflections
**typically a shoulder The zeolite may be yet further characterized by the x-ray diffraction pattern having at least the d-spacings and intensities set forth in Table A3 where the d-spacings and intensities are provided at different relative concentrations of the components of the coherently grown composite structure.

TABLE A3

| I high TUN, low IMF | | | II med TUN, med IMF | | | III low TUN, high IMF | | |
|---|---|---|---|---|---|---|---|---|
| 2-Theta | d(f) | I/Io % | 2-Theta | d(f) | I/Io % | 2-Theta | d(f) | I/Io % |
| 7.21 | 12.25 | w-m | 7.17 | 12.31 | w-m | 7.21 | 12.22 | vw |
| 7.5-8.1* | 11.78-10.91 | w-m | 7.5-8.1* | 11.78-10.91 | w-m | 7.5-8.1* | 11.78-10.91 | w-m |
| 8.88 | 9.95 | m | 8.88 | 9.95 | m-s | 8.88 | 9.95 | m |
| 9.17 | 9.63 | m | 9.16 | 9.65 | m | 9.17** | 9.63 | w-m |
| 9.34** | 9.46 | vw-w | 9.30 | 9.50 | m | 9.33 | 9.47 | m |
| 9.98 | 8.85 | vw | 12.50 | 7.08 | w-m | 12.47 | 7.09 | w-m |
| 11.68 | 7.57 | vw | 15.27 | 5.80 | vw-w | 12.85 | 6.88 | vw |
| 12.62 | 7.00 | w | 15.58 | 5.68 | w | 14.62 | 6.05 | vw-w |
| 13.69 | 6.46 | vw-w | 17.70 | 5.01 | vw-w | 15.27 | 5.80 | w |
| 15.33 | 5.77 | vw-w | 18.72 | 4.74 | vw-m | 15.57 | 5.68 | w |
| 16.48 | 5.37 | vw-w | 19.28 | 4.60 | w | 16.60 | 5.34 | w |
| 17.01 | 5.20 | vw | 22.61** | 3.93 | w-m | 17.70 | 5.01 | vw-w |
| 17.70 | 5.01 | vw-w | 22.8-23.2* | 3.90-3.83 | vs | 18.71 | 4.74 | w-m |
| 19.20 | 4.62 | w-m | 23.43 | 3.79 | s | 19.30 | 4.59 | w |
| 21.59 | 4.11 | vw-w | 24.20 | 3.68 | m | 22.55 | 3.94 | m |
| 22.61** | 3.93 | w-m | 25.12 | 3.54 | m | 22.86** | 3.89 | m-s |

TABLE A3-continued

| I<br>high TUN, low IMF | | | II<br>med TUN, med IMF | | | III<br>low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 22.89 | 3.88 | vs | 26.34 | 3.38 | w-m | 23.03 | 3.86 | vs |
| 23.49 | 3.78 | m | 26.75 | 3.33 | w-m | 23.39 | 3.80 | s |
| 23.93 | 3.72 | vw-w | 28.74-29.25* | 3.10-3.05 | w-m | 24.17 | 3.68 | m |
| 24.13 | 3.68 | m | 35.72 | 2.51 | vw-w | 25.01 | 3.56 | m |
| 24.64 | 3.61 | w | 45.29 | 2.00 | w | 26.19 | 3.40 | vw-w |
| 24.93 | 3.57 | w | 45.62-47.19* | 1.99-1.92 | vw-w | 26.68 | 3.34 | w-m |
| 25.31 | 3.52 | m | | | | 28.76 | 3.10 | w-m |
| 26.62 | 3.35 | w | | | | 35.72 | 2.51 | vw-w |
| 29.10 | 3.07 | w | | | | 45.08 | 2.01 | w |
| 35.72 | 2.51 | vw-w | | | | 45.62-47.19* | 1.99-1.92 | vw-w |
| 45.08 | 2.01 | w | | | | | | |
| 45.62-47.19* | 1.99-1.92 | vw-w | | | | | | |

*composite peak consisting of multiple overlapping reflections
**Typically a shoulder In Tables A2 and A3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

As will be shown in detail in the examples, the UZM-39 material is thermally stable up to a temperature of at least 600° C. and in another embodiment, up to at least 800° C. Also as shown in the examples, the UZM-39 material may have a micropore volume as a percentage of total pore volume of greater than 60%.

Characterization of the UZM-39 product by high-resolution scanning electron microscopy shows that the UZM-39 forms in lathes which assemble into rectangular rod particles, often with a starburst cluster arrangement. The starburst cluster rods of UZM-39 can be seen in the scanning electron microscopy results for two particular UZM-39 products in FIG. 7 and in FIG. 8.

Figure 9:
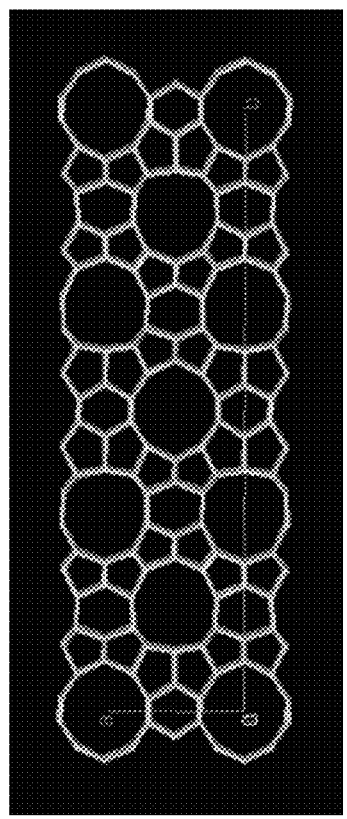
FIG. 9 shows a wireframe representation of the TUN framework in the AC plane (left). Each vertex is a T-site and in the middle of each stick is an oxygen atom. A wireframe representation of the IMF framework in the AB plane is shown to the right. Along these projections, both the TUN and IMF frameworks contain nearly identical projections of chains of 5-rings connected by 6-rings and 10-ring channels.
Figure 9:
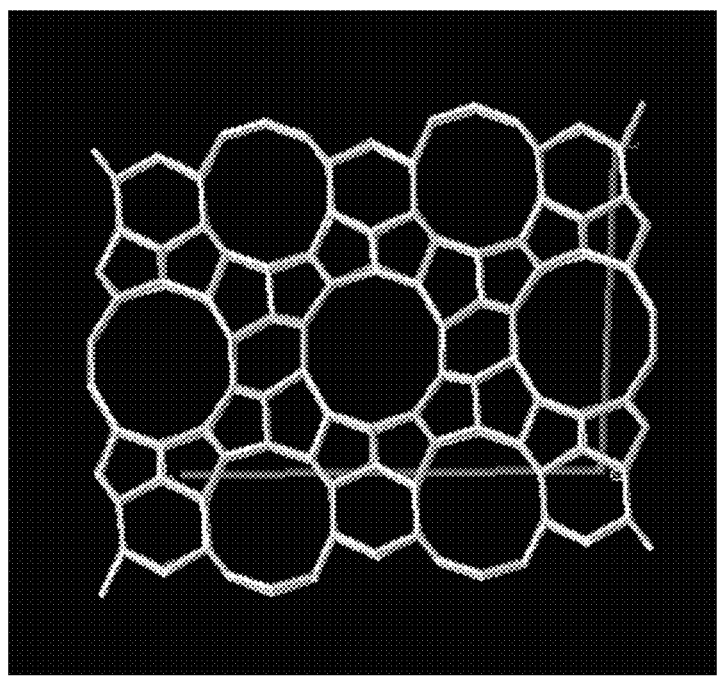

UZM-39 is a coherently grown composite structure of TUN and IMF zeotypes. By coherently grown composite structure is meant that both structures are present in a major portion of the crystals in a given sample. This coherently grown composite structure is possible when the two zeotypic structures have nearly identical spacial arrangements of atoms along at least a planar projection of their crystal structure and possess similar pore topologies. FIG. 9 shows a wireframe representation of the TUN framework in the AC plane (left). Each vertex is a tetrahedral site (or T-site) and in the middle of each stick is a corner-shared oxygen atom. A wireframe representation of the IMF framework in the AB plane is shown on the right of FIG. 9. Along these projections, both the TUN and IMF zeotypes contain nearly identical projections of chains of 5-rings connected by 6-rings and 10-rings which form channels running perpendicular to the plane.

As both the TUN and IMF zeotypes are 3-dimensional 10-ring zeolites and have nearly identical projections in one plane, the two structures can thereby coherently grow off crystals of the other structure with interfaces at the compatible planes to form a coherently grown composite structure.

A coherently grown composite structure is not a physical mixture of the two molecular sieves. Electron diffraction, transmission electron microscopy and x-ray diffraction analysis are employed to show that a material is a coherently grown composite structure instead of a physical mixture. Usually the combination of electron diffraction and TEM imaging is most definitive in determining whether one has produced a coherently grown composite structure because it provides direct evidence of the existence of both structures within one crystal.

Since the coherently grown composite structure zeolites of this invention can have varying amounts of the two structure types, it is to be understood that the relative intensity and line width of some of the diffraction lines will vary depending on the amount of each structure present in the coherently grown composite structure. Although the degree of variation in the x-ray powder diffraction patterns is theoretically predictable for specific structures, the more likely mode of a coherently grown composite structure is random in nature and therefore difficult to predict without the use of large hypothetical models as bases for calculation.

Unlike a physical mixture of TNU-9 and IM-5, transmission electron microscopy (TEM) analysis using high resolution imaging and computed optical diffractograms shows that UZM-39 is comprised of a coherently grown composite structure of TUN and IMF zeotypes.

Figure 10:
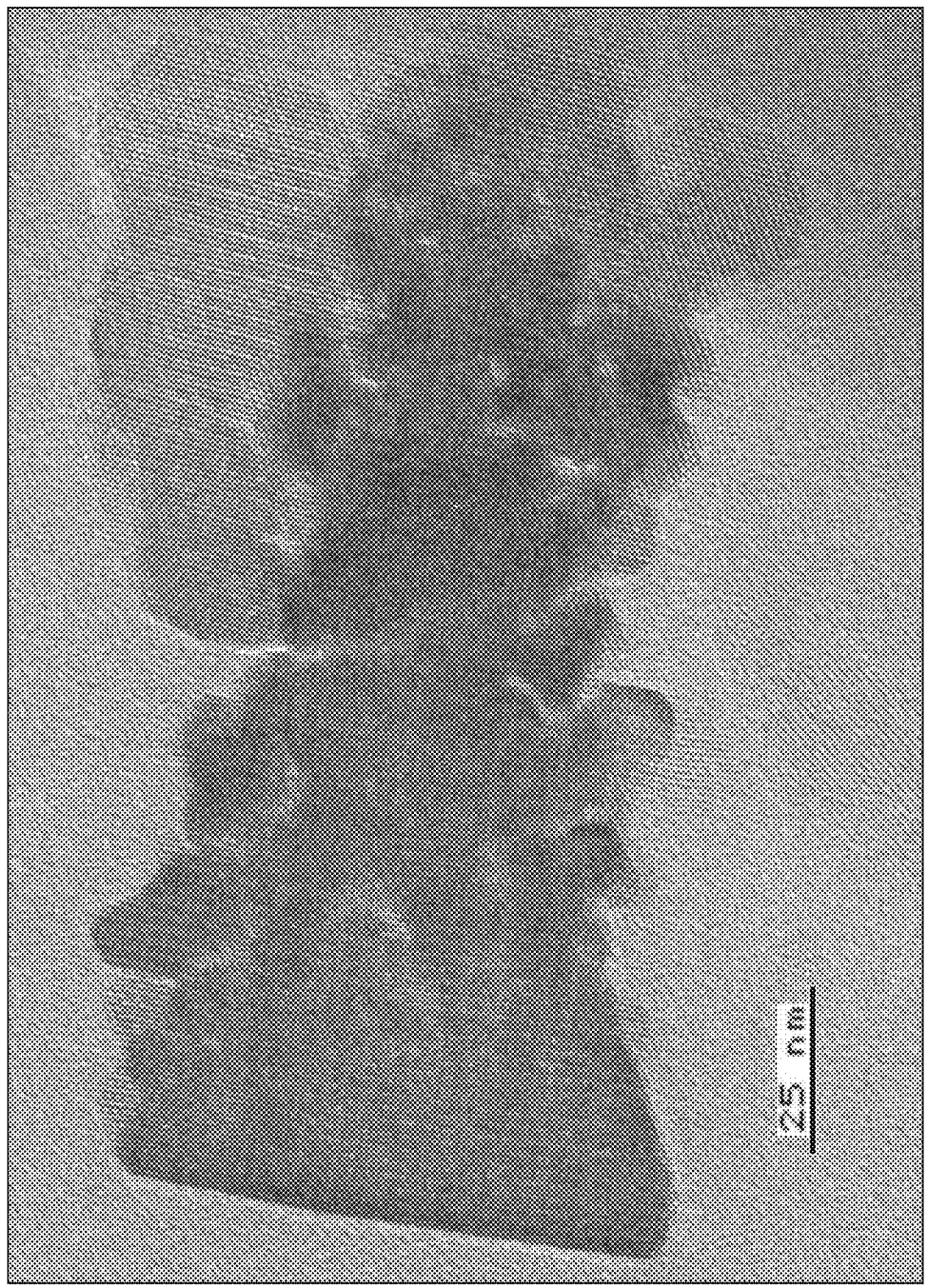
FIG. 10 shows the results of transmission electron microscopy characterization of the UZM-39 product of Example 17 using high resolution imaging and computed optical diffractograms. The results show that UZM-39 is comprised of a coherently grown composite structure of TUN and IMF zeotypes.

In FIG. 10, TEM analysis of a cross sectioned rod particle from the product of Example 17 shows that areas with TUN and IMF structure occur as coherent sub-regions within an effectively single-crystalline zeolite particle. On the left side of FIG. 11, electron diffraction analysis of the left side of the particle shown in FIG. 10 shows an electron diffraction pattern which can be indexed to the 002 plane of TUN. On the right side of FIG. 11, the electron diffraction pattern from the right side of the particle shown in FIG. 10 is shown. This pattern can be indexed to the 060 plane of IMF. The TUN regions and IMF regions are coherently aligned such that the $[010]_{TUN}$ zone axis and the $[001]_{IMF}$ zone axis are parallel to each other and there is continuity of crystal planes of type $(002)_{TUN}$ and $(060)_{IMF}$, where the indexing is referred to monoclinic $C_{2/m}$ and orthorhombic $C_{mcm}$ unit cells for TUN and IMF respectively (details of structures found on IZA website). In spite of the presence of the two zeotypes in different portions of the particle, the image does not show any distinct boundary delineating separate crystals of TUN and IMF, indicating that the particle is a coherently grown composite.

Additionally, UZM-39 zeolite can be characterized by Rietveld analysis of the XRD pattern. Rietveld analysis is a least-squares approach developed by Rietveld (*Journal of Applied Crystallography* 1969, 2: 65-71) to refine a theoretical line XRD profile until it matches the measured XRD pattern as closely as possible and is the preferred method of deriving structural information from samples such as UZM-39 which contain strongly overlapping reflections. It is often used to quantify the amounts of two different phases in a XRD diffractogram. The accuracy of the Rietveld method is determined by parameters such as crystallite size (peak broadening), peak shape function, lattice unit cell constants and background fits. For the samples shown in the examples, applicants have determined the error in the reported value to be ±5% under the conditions used. Applicants have also determined that the Rietveld model used was unable to quantify the amounts of minority composite structure phase components at values less than 10%, but visually, amounts of the minority components can be seen at levels greater than 5% by comparing against the model patterns. Table 1 shows Rietveld refinement results on various UZM-39 samples from the examples and shows that UZM-39 contains greater than 0 and less than 100 wt. % IMF zeotype and less than 100 wt. % and greater than 0 wt. % TUN zeotype. In another embodiment, UZM-39 contains greater than 5 and less than 95 wt. % IMF zeotype and less than 95 wt. % and greater than 5 wt. % TUN zeotype, and in yet another embodiment, UZM-39 contains greater than 10 and less than 90 wt. % IMF zeotype and less than 90 wt. % and greater than 10 wt. % TUN zeotype. As can be seen in Table 1 and examples, a wide range of coherently grown composite structures are possible by modifying the synthesis conditions.

As synthesized, the UZM-39 material will contain some exchangeable or charge balancing cations in its pores. These exchangeable cations can be exchanged for other cations, or in the case of organic cations, they can be removed by heating under controlled conditions. It is also possible to remove some organic cations from the UZM-39 zeolite directly by ion exchange. The UZM-39 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the microporous crystalline zeolite UZM-39 has a three-dimensional framework of at least $AlO_2$ and $SiO_2$ tetrahedral units and an empirical composition in the hydrogen form expressed by an empirical formula of $$M1_a^{N+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

In the hydrogen form, after calcination, ion-exchange and calcination to remove $NH_3$, UZM-39 displays the XRD pattern shown in Table B1-B3. Those peaks characteristic of UZM-39 are shown in Tables B1-B3 for various coherently grown composite structures. Additional peaks, particularly those of very weak intensity, may also be present. All peaks of medium or higher intensity present in the UZM-39 family of coherently grown composite structures are represented in at least Tables B3.

Table B1 contains selected d-spacings and relative intensities of the hydrogen form of UZM-39 X-ray diffraction pattern. The relative intensities are shown as a range covering UZM-39 materials with varying relative amounts of TUN and IMF zeotypes.

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections

The zeolite may be further characterized by the x-ray diffraction pattern having at least the d-spacings and intensities set forth in Table B2 where the d-spacings and intensities are provided at different relative concentrations of the components of the coherently grown composite structure.

TABLE B2

| A high TUN, low IMF | | | B med TUN, med IMF | | | C low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 12.48 | 7.09 | m | 12.46 | 7.10 | m |
| 22.89 | 3.88 | vs | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 24.23 | 3.67 | w-m | 23.40 | 3.80 | s | 23.40 | 3.80 | s |
| 25.22 | 3.53 | m | 24.17 | 3.68 | m | 24.12 | 3.69 | m |

TABLE B2-continued

| A high TUN, low IMF | | | B med TUN, med IMF | | | C low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 29.08 | 3.07 | w-m | 24.92-25.37* | 3.57-3.51 | m | 25.06 | 3.55 | m |
| 45.36 | 2.00 | w | 28.71-29.27* | 3.11-3.05 | w-m | 28.82 | 3.10 | w-m |
| | | | 45.34 | 2.00 | w | 45.32 | 2.00 | w |

*composite peak consisting of multiple overlapping reflections
**Typically a shoulder The zeolite may be yet further characterized by the x-ray diffraction pattern having at least the d-spacings and intensities set forth in Table B3 where the d-spacings and intensities are provided at different relative concentrations of the components of the coherently grown composite structure.

TABLE B3

| I high TUN, low IMF | | | II med TUN, med IMF | | | III low TUN, high IMF | | |
|---|---|---|---|---|---|---|---|---|
| 2-Theta | d(Å) | I/Io % | 2-Theta | d(Å) | I/Io % | 2-Theta | d(Å) | I/Io % |
| 7.12 | 12.40 | w-m | 7.11 | 12.42 | w-m | 7.16 | 12.25 | vw-w |
| 7.5-8.1* | 11.78-10.91 | m | 7.5-8.1* | 11.78-10.91 | m-s | 7.5-8.1* | 11.78-10.91 | m-s |
| 8.84 | 10.00 | m-s | 8.84 | 10.00 | m-s | 8.84 | 10.00 | m-s |
| 9.06 | 9.75 | m | 9.08 | 9.73 | m | 9.06** | 9.75 | w |
| 9.24** | 9.56 | vw-w | 9.24 | 9.56 | m | 9.24 | 9.56 | m |
| 12.53 | 7.06 | w | 11.76 | 7.52 | vw-w | 11.76 | 7.52 | vw-w |
| 14.38 | 6.15 | w | 12.48 | 7.09 | m | 12.46 | 7.10 | m |
| 14.64 | 6.05 | vw | 14.38 | 6.15 | vw-w | 14.38 | 6.15 | vw |
| 15.26 | 5.80 | vw-w | 14.64 | 6.05 | vw-w | 14.64 | 6.05 | w |
| 15.52 | 5.70 | vw | 15.26 | 5.80 | w | 15.26 | 5.80 | w |
| 16.46 | 5.38 | vw | 15.52 | 5.70 | w-m | 15.52 | 5.70 | w-m |
| 17.72 | 5.00 | w | 16.50 | 5.37 | vw-w | 16.58 | 5.34 | w |
| 22.56** | 3.94 | vw-w | 17.72 | 5.00 | w-m | 17.72 | 5.00 | w-m |
| 22.89 | 3.88 | vs | 18.64 | 4.76 | vw-w | 18.64 | 4.76 | w |
| 23.06** | 3.85 | w-m | 22.56** | 3.94 | w-m | 22.56 | 3.94 | w-m |
| 23.40 | 3.80 | m | 22.75-23.2* | 3.90-3.83 | vs | 23.06 | 3.85 | vs |
| 23.82 | 3.73 | w-m | 23.40 | 3.80 | s | 23.40 | 3.80 | s |
| 24.23 | 3.67 | w-m | 24.17 | 3.68 | m | 24.12 | 3.69 | m |
| 24.70 | 3.60 | w-m | 24.70 | 3.60 | w-m | 25.06 | 3.55 | m |
| 25.22 | 3.53 | m | 24.92- 25.37* | 3.57-3.51 | m | 26.16 | 3.40 | vw-w |
| 26.51 | 3.36 | w-m | 26.32 | 3.38 | w | 26.74 | 3.33 | w-m |
| 29.08 | 3.07 | w-m | 26.76 | 3.33 | w-m | 28.82 | 3.10 | w-m |
| 35.86 | 2.50 | vw-w | 28.71-29.27* | 3.11-3.05 | w-m | 30.12 | 2.96 | w |
| 45.36 | 2.00 | w | 30.13 | 2.96 | vw-w | 35.86 | 2.50 | vw-w |
| 45.66-47.37* | 1.98-1.91 | vw-w | 35.86 | 2.50 | vw-w | 45.32 | 2.00 | w |
| | | | 45.34 | 2.00 | w | 45.66- 47.37* | 1.98-1.91 | vw-w |
| | | | 45.66-47.37* | 1.98-1.91 | vw-w | | | |

*composite peak consisting of multiple overlapping reflections
**Typically a shoulder In Tables B2 and B3, the term "high" refers to about 60 to about 95 mass-% of the specified component, the term "med" refers to about 25 to about 70 mass-% of the specified component, and the term "low" refers to about 5 to about 40 mass-% of the specified component. Some peaks may be shoulders on more intense peaks, and some peaks may be a composite peak consisting of multiple overlapping reflections.

After acid treating, such as exposure to $HNO_3$ or $H_2SiF_6$, and on an anhydrous basis, the microporous crystalline zeolite UZM-39 has a three-dimensional framework of at least $AlO_2$ and $SiO_2$ tetrahedral units and an empirical composition in the acid treated form expressed by an empirical formula of

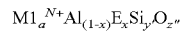

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of 0 to (Al+E) and has a value determined by the equation:

$$z''=(a \cdot N+3+4 \cdot y')/2$$

Similar to the as-synthesized material, the modified UZM-39 materials are thermally stable up to a temperature of at least 600° C. and in another embodiment, up to at least 800° C. and may have a micropore volume as a percentage of total pore volume of greater than 60%.

By virtually pure silica is meant that virtually all the aluminum and/or the E metals have been removed from the framework. It is well known that it is virtually impossible to remove all the aluminum and/or E metal. Numerically, a zeolite is virtually pure silica when y' has a value of at least 3,000, preferably 10,000 and most preferably 20,000. Thus, ranges for y' are from 9 to 3,000; from greater than 20 to about 3,000; from 9 to 10,000; from greater than 20 to about 10,000; from 9 to 20,000; and from greater than 20 to about 20,000. In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-39 zeolite is used as a catalyst or catalyst support in various reactions. The catalyst composite comprising UZM-39 zeolite and modifications thereof can be used as a catalyst or catalyst support in processes for the conversion of low carbon number aliphatic hydrocarbons to generate higher carbon number hydrocarbons. The catalytic composite may further comprise a promoter selected from the group consisting of iron, cobalt, vanadium, manganese, gallium, zinc, chromium, tungsten, molybdenum and combinations thereof. The promoter metal can be dispersed on the porous support by means well known in the art such as impregnation, spray-drying, ion-exchange, vapor deposition, etc. Impregnation of the support with the promoter metal can be carried out using decomposable compounds of the promoter metals. By "decomposable compound" is meant that upon heating the compound decomposes to give the corresponding metal or metal oxides. Examples of the compounds of iron, cobalt, vanadium, manganese, or molybdenum tungsten which can be used include the halides, nitrates, sulfates, phosphates, carbonates, acetates and oxalates. Other examples of molybdenum compounds which can be used include molybdates such as ammonium hexamolybdate, 12-phosphomolybdic acid, 12-silicomolybdic acid and 12-phosphomolybdic vanadic acid, $MoS_3$, $Mo(CO)_6$, $[Mo_3(CH_3C)(O)(CH_3COO)_9]X(X=Cl, Br$ and $I)$ and $(Mo_2(CH_3COO)_6$ and combinations thereof. Any soluable tungsten containing compound may be used. A particular tungsten compound which can be used is ammonium metatungstate. It should be pointed out that both deposition and ion-exchange of the metals can occur. Therefore, in the present context, impregnation will encompass ion-exchange as well as conventional impregnation. The impregnation is carried out with a solution containing at least one metal compound followed by calcination at a temperature of about 50° C. to about 800° C. for a time of about 5 minutes to about 10 hr. Next, the calcined catalyst may be activated by treating the catalyst with a hydrogen/and/or methane treatment gas at a temperature of about 100° C. to about 800° C. for a time of about 5 minutes to about 10 hr. The amount of promoter metal which is dispersed in the final catalyst can vary considerably, but usually the promoter metal varies from about 0.001 wt. % to about 25 wt. % of the catalytic composite.

The UZM-39 catalyst composite may further comprise a refractory inorganic-oxide binder. The UZM-39 may be mixed with a binder for convenient formation of catalyst particles in a proportion of about 5 to 100 mass % UZM-39 zeolite and 0 to 95 mass % binder, with the UZM-39 zeolite typically comprising from about 10 to 90 mass % of the composite. In one embodiment, the binder is porous, has a surface area of about 5 to about 800 $m^2/g$, and is relatively refractory to the conditions utilized in the hydrocarbon conversion process. Non-limiting examples of binders are silica, aluminas, titania, zirconia, zinc oxide, magnesia, boria, thoria, chromia, stannicoxide, as well as combinations and composites thereof, for example, silica-alumina, silica-magnesia, silica-zirconia, chromia-alumina, alumina-boria, alumina-titainia, aluminophosphates, silica-zirconia, silica gel, and clays. In one embodiment the binder is one or more of amorphous silica and alumina, including gamma-, eta-, and theta-alumina. In another embodiment the binder is gamma- and or eta-alumina Alumina may be employed as the refractory inorganic oxide for use herein, and the alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like.

The binder and zeolite may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. One method comprises commingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

In one embodiment the shapes are extrudates and or spheres. Extrudates are prepared by conventional means which involves mixing of the composition either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50 to about 200° C. and subjected to a calcination procedure at a temperature of about 450 to about 700° C. for a period of about 1 to about 20 hours. This treatment effects conversion of the hydrogel to the corresponding alumina matrix.

The catalyst of the invention optionally may comprise an additional zeolitic component, The additional zeolite component preferably is selected from one or more of MFI, MEL, EUO, FER, MFS, MOR, MTT, MTW, MWW, MAZ, TON, TUN, IMF, SVR, SZR, and FAU (Atlas Structure Commission of International Zeolite Association) and UZM-8 (see WO 2005/113439). Suitable total zeolite amounts in the catalyst range from about 1 to about 100 wt-%, preferably from about 10 to about 95 wt-%, and more preferably between about 60 and about 90 wt-%.

The catalytic composite is employed in a process for converting low carbon number aliphatic hydrocarbons to higher carbon number hydrocarbons. More specifically, the process is a dehydroaromatization process in which low carbon number aliphatic compounds such as methane are converted to aromatic compounds such as benzene and naphthalene plus ethylene. Since dehydrogenation is part of the reaction, hydrogen is produced during the process. By low carbon number aliphatic hydrocarbons is meant any aliphatic hydrocarbon having from 1 to about 4 carbon atoms. The feedstream which can be used in the process of the invention can be any feedstream which contains at least 5 mass-% of an aliphatic hydrocarbon having from 1 to about 4 carbon atoms. In another embodiment the feedstream contains at least 20 mass-% of an aliphatic hydrocarbon having from 1 to about 4 carbon atoms. In another embodiment, the feedstream contains at least 50 mass-% of aliphatic hydrocarbons having from 1 to about 4 carbon atoms. In one embodiment the low carbon number aliphatic hydrocarbon is methane. In one embodiment, in addition to at least 5 mass-% methane, the feedstream may also contain $C_2$-$C_4$ saturated hydrocarbons such as ethane, propane, n-butane, isobutane, etc. In one embodiment. In one embodiment, in addition to at least 5 mass-% methane, the feedstream may also contain $C_2$-$C_4$ unsaturated hydrocarbons such as ethylene, acetylene, propylene, butene, isobutene, etc. The feed stream may further comprise diluents such as hydrogen, nitrogen, or argon. The feed stream may comprise from greater than zero to 100 wt % methane. The feed stream may comprise from about 50 wt % to 100 wt % methane. The feed stream may comprise from about 80 wt % to about 90 wt % methane. The feed stream may comprise from about 80 wt % to greater than 99 wt % methane.

The feedstream is contacted with the catalyst comprising UZM-39 at conversion conditions either in a batch mode or a continuous flow mode. In the continuous flow mode, the catalyst can be present as a fixed bed, moving bed, or fluidized bed. The process is carried out by contacting the feedstream in the absence of oxygen at a temperature of about 300° C. to about 1000° C. and in another embodiment, from about 450° C. to about 900° C., a pressure of about 10 kPa to about 1000 kPa and in another embodiment from about 100 to about 1000 kPa and a gas hourly space velocity in the range of about 100 to about 200,000 $hr^{-1}$. The reaction zone may further contain CO, $CO_2$ or mixtures thereof, in order to improve catalyst performance. The CO, $CO_2$ or mixtures thereof to aliphatic hydrocarbon mole ratio varies from about 0.001 to about 0.5 and in another embodiment from about 0.01 to about 0.3.

A particular benefit of the invention is the stability of the catalyst comprising UZM-39 at temperatures above about 550° C., above, 600° C., above 650° C., above 700° C. or above 750° C. in an oxygen-containing environment. The effluent from the reaction zone can be separated by conventional means and the unreacted feedstream components recycled to the reaction zone.

During regeneration operations at high temperatures, such as greater than 500° C., in an oxygen containing atmosphere designed to burn coke, the promoter metal, such as molybdenum, may interact with the zeolites which results in deactivation of the zeolite. One technique possible to minimize deactivation of the zeolite during regeneration is performing the regeneration at low temperatures, such as less than 500° C. However, operationally is it difficult and costly to operate a commercial process with temperature swing between the process of dehydroaromatization, which may require temperatures greater than 700° C., and catalyst regeneration if it is performed at less than 500° C. A benefit of the process herein is improved stability of the catalyst, which allows for regeneration of the catalyst either at the same temperature as dehydroaromatization, or with a minimal temperature swing such as less than 50° C. By providing a more temperature tolerant catalyst, the process solves the problem of zeolite deactivation during regeneration while at the same time provides the benefit of desirable and less costly operations with regeneration temperatures that are closer to the conversion temperatures.

Catalysts suitable for the conversion of at least one low carbon number hydrocarbon in a feedstream to provide at least one aromatic hydrocarbon may comprise a zeolite which is temperature tolerant. Following incorporation of the promoter metal, such as molybdenum or tungsten, temperature tolerant zeolites may be those characterized by the retention, as evidenced by quantitative solid state $^{27}Al$ NMR, of greater than 40% of the tetrahedral aluminum sites in the zeolite following calcination of the catalyst in air at 750° C. for 3 hours when compared to the amount of tetrahedral aluminum in the same catalyst after calcination in air at 500° C. for 3 hours. A zeolite may by characterized by 81 mol % tetrahedral aluminum by $^{27}Al$ solid state NMR after incorporation of a promoter metal such as molybdenum and calcination of the resulting catalyst at 500° C. for 3 hours in air. The same promoter incorporated zeolite may instead by calcined at 750° C. for 3 hours in air and be characterized by 61 mol % tetrahedral aluminum. This zeolite thus demonstrates 75.3% retention of the tetrahedral aluminum sites in the zeolite. In an embodiment, the retention of tetrahedral aluminum sites in the zeolite may be greater than 50% or greater than 65% or greater than 70% or greater than 75% or greater than 80% following calcination of the catalyst in air at 750° C. for 3 hours when compared to the amount of tetrahedral aluminum in the same catalyst after calcination in air at 500° C. for 3 hours. The retention of tetrahedral aluminum sites in the zeolite may be greater than 25% following calcination of the catalyst in air at 750° C. for 3 hours when compared to the amount of tetrahedral aluminum in the zeolite prior to incorporation of the promoter metal. In an embodiment, the retention of tetrahedral aluminum sites in the zeolite may be greater than 35% or greater than 50% or greater than 65% or greater than 70% or greater than 80% following calcination of the catalyst in air at 750° C. for 3 hours when compared to the amount of tetrahedral aluminum in the zeolite prior to incorporation of the promoter metal. The zeolite may be characterized by formation of less than 3.0 mol % or less than 2.0 mol % or less than 1.0 mol % aluminum metalate $Al_2(MO_4)_3$, after calcination of the metal incorporated zeolite at 500° C. for 3 hours in air, where M is Mo or W, as evidenced by quantitative solid state $^{27}Al$ NMR. The zeolite may be characterized by the formation of essentially no aluminum metalate, i.e., an undetectable quantity of aluminum metalate. The zeolite may be characterized by formation of less than 15 mol % or less than 10 mol % or less than 5 mol % or less than 1 mol % aluminum metalate $Al_2(MO_4)_3$, after calcination of the metal incorporated zeolite at 750° C. for 3 hours in air, where M is Mo or W, as evidenced by quantitative solid state $^{27}Al$ NMR. The zeolite may be characterized by the formation of essentially no aluminum metalate, i.e., an undetectable quantity of aluminum metalate. Following incorporation of the promoter metal, such as molybdenum or tungsten, suitable zeolites may be those characterized by the retention, as evidenced by pyridine IR, of greater than 15% of the Broensted acid sites in the zeolite following calcination of the catalyst in air at 750° C. for 3 hours when compared to the amount of Broensted acid sites in the same catalyst after calcination in air at 500° C. for 3 hours. The retention of Broensted acid sites in the zeolite may be greater than 15% following calcination of the catalyst in air at 750° C. for 3 hours when compared to the amount of Broensted acid sites in the same catalyst prior to incorporation of the promoter metal. In an embodiment, the retention of Broensted acid sites may be greater than 25% or greater than 30% or greater than 35% or greater than 40%. Pyridine IR is generally carried out via the methods described by Parry in J. Catal. 1963, 2, 371-9 using a 150° C. desorption temperature and integrating the peak at 1540 cm$^{-1}$ to quantify the Broensted acidity. In an embodiment, the zeolite may be characterized by any combination of or all of the characteristics set forth in the preceding paragraph.

The following examples are presented in illustration of this invention and are not intended as undue limitations on the generally broad scope of the invention as set out in the appended claims. The structure of the UZM-39 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

$vw = <5; w = 6-15; m = 16-50; s = 51-80;$ and $vs = 80-100$

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

A sample of UZM-39 was prepared as follows. 6.02 g of NaOH, (97%) was dissolved in 125.49 g water. 0.62 g Al (OH)$_3$, (29.32 wt.-% Al) was added to the NaOH solution to form a first solution. Separately, 0.24 g of the layered material UZM-8 was stirred into 30.0 g Ludox AS-40 to form a second solution. The second solution was added to the first solution. The mixture was cooled to 0° C.-4° C. Separately, 6.54 g 1,4-dibromobutane, (99 wt.-%) was mixed with 7.65 g 1-methylpyrrolidine, (97 wt.-%) to form a third solution. The third solution was added to the cooled mixture of the first and second solutions to form the final reaction mixture. The final reaction mixture was transferred to a 300 cc stirred autoclave and digested at 160° C. for 144 hours with stirring at 100 rpm. The product was isolated by filtration. The product was identified as UZM-39 by XRD as shown in FIG. 1. Analytical results show this material has the following molar rations: Si/Al of 12.64, Na/Al of 0.116, N/Al of 0.92, C/N of 7.23.

Figure 2:
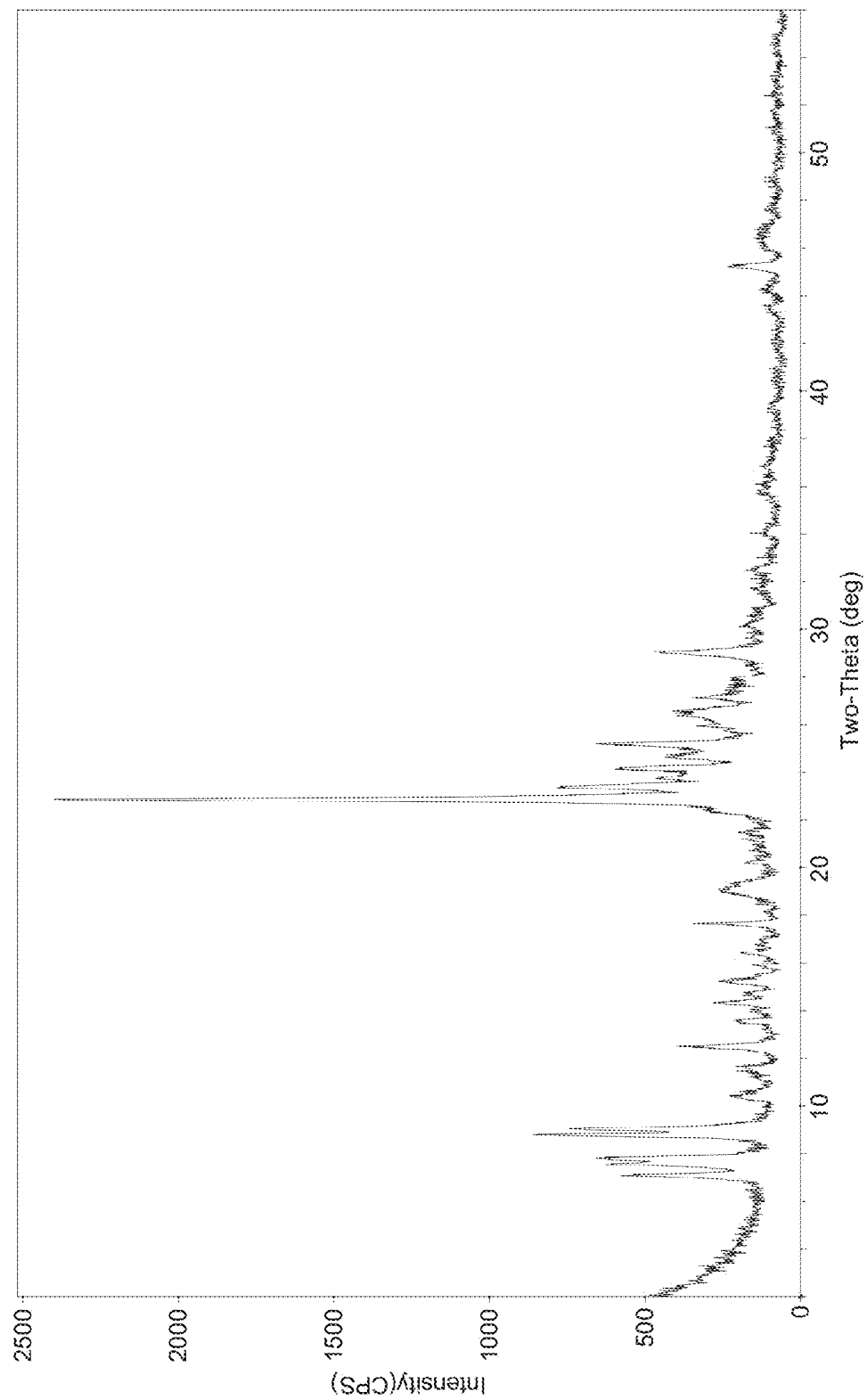
FIG. 2 is also an XRD pattern of the UZM-39 zeolite formed in Example 1. This pattern shows the UZM-39 zeolite after calcination.
Figure 7:
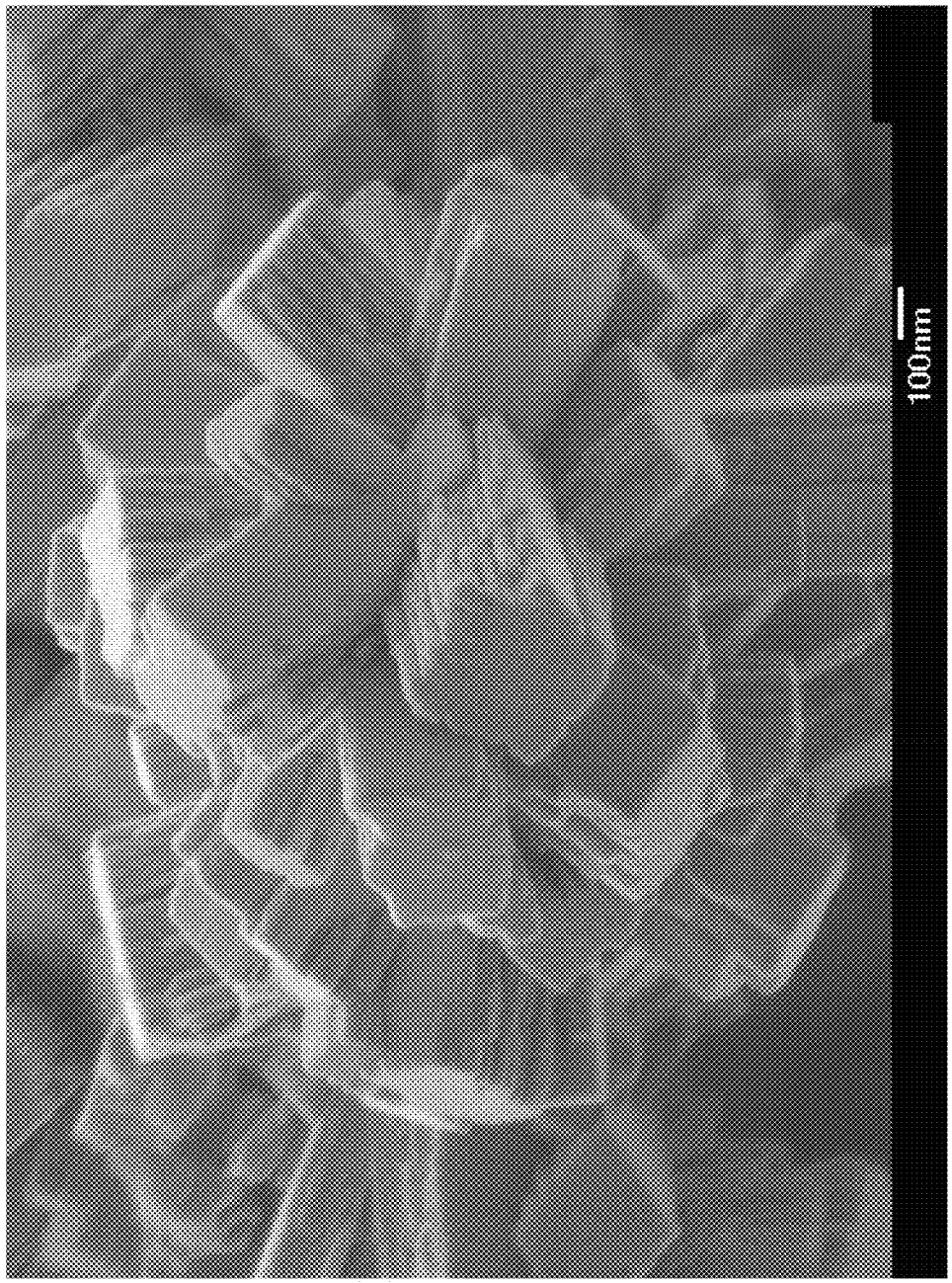
FIG. 7 shows the results of high-resolution scanning electron microscopy characterization of the UZM-39 product of Example 1. The electron micrograph shows that UZM-39 forms in lathes which assemble into rectangular rod particles, often with a starburst cluster arrangement. The starburst cluster rods of UZM-39 can be seen in the scanning electron microscopy results of FIG. 7.

Scanning Electron Microscopy (SEM) revealed crystals of intergrown, square rod morphology in starbursts, approximately 250 to 700 nm along a face of the square with an aspect ratio of from 2:1 to 5:1. The micrograph is shown in FIG. 7. The product was calcined at 550° C. for 3 hrs under air. The XRD pattern of the calcined material is shown in FIG. 2.

Comparative Example 2

The preparation of Example 1 was followed, except that the layered material UZM-8 was not added to the second solution. After 144 hours of stirring at 100 rpm at 160° C., the product was isolated by filtration. The product was identified as analcime by XRD.

Comparative Example 3

6.68 g of NaOH, (97%) was dissolved in 145.44 g water. 2.86 g Al(NO$_3$)$_3$.9H$_2$O (97%) was added to the sodium hydroxide solution. 13.33 g Aerosil 200 was stirred into the mixture. 13.1 g H$_2$O was added. 7.26 g 1,4-dibromobutane, (99%) and 5.84 g 1-methylpyrrolidine, (97%) were added and the mixture was stirred vigorously for a day. The mixture was divided equally and loaded into eight 45 cc Parr vessels and placed into a rotisserie oven at 160°. The mixture in one of the Parr vessels produced a material at 256 hours identified by XRD as having the TUN structure. Analytical results showed this material to have the following molar ratios, Si/Al of 15.51, Na/Al of 0.12, N/Al of 1.29, and C/N of 6.89. SEM analysis revealed a squat rod cluster morphology, about 300-800 nm in length and with an aspect ratio of about 1.

The product generated by this synthesis was calcined under flowing air at 600° for 6 hours. It was then ion exchanged four times with 1 M ammonium nitrate solution at 75° followed by a calcination at 500° under air for 2 hours to convert NH$_4^+$ into H$^+$.

Analysis for the calcined, ion-exchanged sample showed 39.2 wt. % Si, 2.34 wt. % Al, <0.005 wt. % Na with a BET surface area of 378 m$^2$/g, pore volume of 0.220 cm$^3$/g, and micropore volume of 0.190 cm$^3$/g.

Analysis of the H+-form of this material by Rietveld XRD refinement showed that the material consisted entirely of TUN structure type. TEM analysis confirmed that no coherent growth of IMF crystals occurred.

Example 4

6.40 g of NaOH, (97%) was dissolved in 111.88 g water. 1.16 g Al(OH)$_3$, (29.32 wt.-% Al), was added to the sodium hydroxide solution to create a first solution. Separately, 0.30 g of the layered material (UZM-8) was stirred into 37.5 g Ludox AS-40 to form a second solution. The second solution was added to the first solution and vigorously stirred for 1-2 hours. The mixture was cooled to 0° C.-4° C. Separately, 8.18 g 1,4-dibromobutane, (99 wt.-%) was mixed with 9.56 g 1-methylpyrrolidine, (97 wt.-%) to form a third solution. The third solution was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 12.07, Na/Al of 0.124, N/Al of 0.90, C/N of 6.85.

Example 5

7.19 g of NaOH, (99 wt.-%%) was dissolved in 90.1 g water. 1.56 g Al(OH)$_3$, (29.32 wt.-% Al), was added to the sodium hydroxide solution to create a first solution. Separately, 0.405 g of the layered material (UZM-8) was stirred into 50.62 g Ludox AS-40 to form a second solution. The second solution was added to the first solution and vigorously stirred for 1-2 hours. The mixture was cooled to 0° C.-4° C. Separately, 11.04 g 1,4-dibromobutane, (99 wt.-%), was mixed with 12.90 g 1-methylpyrrolidine, (97 wt.-%) to form a third solution. The third solution was added to the cooled mixture to create the final reaction mixture. The final reaction mixture was vigorously stirred for 5 minutes and transferred to a 300 cc stirred autoclave. The final reaction mixture was digested at 160° C. for 144 hours with stirring at 100 rpm. 16.5 g of the product was isolated by filtration. The product was identified by XRD to be UZM-39 with a very slight MOR impurity. Analytical results showed this material to have the following molar ratios, Si/Al of 14.14, Na/Al of 0.16, N/Al of 1.02, C/N of 7.33.

Example 6

37.62 g of NaOH, (97 wt.-%) was dissolved in 600 g water to create a sodium hydroxide solution. 6.96 g Al(OH)$_3$ (29.32 mass % Al) was added to the sodium hydroxide solution to create a first solution. Separately, 1.80 g of the layered material (UZM-8) was stirred into 225 g Ludox AS-40 to form a second solution. The second solution was added to the first solution and vigorously stirred for 1-2 hours. The mixture was cooled to 0° C.-4° C. Separately, 49.08 g 1,4-dibromobutane (99 wt.-%) was mixed with 57.36 g 1-methylpyrrolidine (97 wt.-%) for 1-5 minutes to form a third solution. The third solution was added to the cooled mixture to create the final reaction mixture. The final reaction mixture was vigorously stirred for 5 minutes and transferred to a 2 liter stirred autoclave. The final reaction mixture was digested at 160° C. for 144 hours with stirring at 250 rpm. The product was isolated by filtration. The product was identified by XRD as UZM-39. Analytical results showed this material to have the following molar ratios, Si/Al of 11.62, Na/Al of 0.12, N/Al of 0.88, C/N of 7.36.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis of the $H^+$ form of this material by Rietveld XRD refinement gave the results shown in Table 1.

Example 7

505.68 g of NaOH, (99 wt.-%) was dissolved in 10542 g water. 52.08 g Al(OH)$_3$, (29.3 wt.-% Al), was added to the sodium hydroxide solution to create a first solution. Separately, 20.16 g of the layered material (UZM-8) was stirred into 2520 g Ludox AS-40 to form a second solution. The second solution was added to the first solution and vigorously stirred for 1-2 hours. The mixture was cooled to 0° C.-4° C. Separately, 549.36 g 1,4-dibromobutane (99 wt.-%) was mixed with 642.6 g 1-methylpyrrolidine, (97 wt.-%), for 3-5 minutes to form a third solution. The third solution was added to the cooled mixture to create the final reaction mixture. The final reaction mixture was vigorously stirred for 5 minutes and pumped into a 5 gallon stirred autoclave. The final reaction mixture was digested at 160° C. for 150 hours with stirring at 100 rpm. The product was isolated by filtration. The product was identified by XRD as UZM-39. Analytical results showed this material to have the following molar ratios, Si/Al=13.35, Na/Al=0.087, N/Al=0.96, C/N=7.12.

Example 8

The preparation of Example 4 was followed except that UZM-8 was replaced with 0.30 g UZM-26. The product was identified by XRD as UZM-39. Analytical results showed this material to have the following molar ratios: Si/Al=12.88, Na/Al=0.25, N/Al=0.88, C/N=7.31.

Example 9

6.27 g of NaOH, (99%), was dissolved in 111.88 g water to create a sodium hydroxide solution. 1.16 g Al(OH)$_3$ (29.32 mass % Al) was added to the sodium hydroxide solution to create a first solution. 37.5 g Ludox AS-40 and then 0.22 g of the layered material UZM-5 were added to the first solution. The first solution was vigorously stirred for 1-2 hours. The first solution was cooled to 0° C.-4° C. Separately, 8.18 g 1,4-dibromobutane (99%) was mixed with 9.56 g 1-methylpyrrolidine (97%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 160° C. for 144 hours with stirring at 100 rpm. The product was isolated by filtration. The product was identified by XRD as UZM-39 with a very small EUO or NES contaminant.

Comparative Example 10

This example is identical to example 4 except that UZM-8 was replaced with 0.30 g UZM-39. The product was identified as a composition comprising MTW, UZM-39, ANA and MOR Example 11

6.27 g of NaOH, (97 wt.-%) was dissolved in 111.88 g water. 1.16 g Al(OH)$_3$, (29.32 wt. % Al), was added to the sodium hydroxide solution to create a first solution. Separately, 0.30 g of the layered material (UZM-8) was stirred into 37.5 g Ludox AS-40 to form a second solution. The second solution was added to the first solution and vigorously stirred for 1-2 hours. The mixture was cooled to 0° C.-4° C. Separately, 12.27 g 1,4-dibromobutane (99 wt.-%) was mixed with 14.34 g 1-methylpyrrolidine (97 wt.-%) to form a third solution. The third solution was added to the cooled mixture to create the final reaction mixture. The final reaction mixture was vigorously stirred and transferred to a 300 cc stirred autoclave. The final reaction mixture was digested at 160° C.

for 144 hours with stirring at 100 rpm. The product was isolated by filtration. The product was identified as UZM-39 with an ESV impurity by XRD. Analytical results showed this material to have the following molar ratios, Si/Al=13.17, Na/Al=0.126, N/Al=1.03, C/N=7.22.

Example 12

The procedure of Example 4 was followed except 9.56 g 1-methylpyrrolidine, (97 wt.-%), was replaced with 8.05 g dimethylethylamine, (97 wt.-%). The product was identified as a composition comprising mordenite and UZM-39.

Example 13

6.27 g of NaOH (99 wt.-%) was dissolved in 111.88 g water. 1.16 g Al(OH)$_3$ (29.32 wt.-% Al) was added to the sodium hydroxide solution to create a first solution. 0.30 g of the layered material UZM-8 and 37.5 g Ludox AS-40 were added to the first solution. The first solution was vigorously stirred for 1-2 hours. The first solution was cooled to 0° C.-4° C. Separately, 4.02 g dimethylethylamine (97 wt.-%) was mixed with 4.78 g 1-methylpyrrolidine (97 wt.-%) for 1-2 minutes to form an amine solution. 8.18 g 1,4-dibromobutane (99 wt.-%) was added to the amine solution and then mixed for 1-2 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 160° C. for 192 hours with stirring at 100 rpm. The product was isolated by filtration. The product was identified as UZM-39 by XRD. Analytical results showed this material to have the following molar ratios, Si/Al=12.42, Na/Al=0.175, N/Al=0.91, C/N=6.92.

The product generated by this synthesis was calcined under flowing air at 600° for 6 hours. It was then ion exchanged four times with 1 M ammonium nitrate solution at 75° followed by a calcination at 500° C. under air for 2 hours to convert NH$_4^+$ into H$^+$. Analysis for the calcined, ion-exchanged sample shows 38.7% Si, 2.97% Al, 0.0089% Na with a BET surface area of 375 m$^2$/g, pore volume of 0.238 cm$^3$/g, and micropore volume of 0.184 cm$^3$/g. Analysis of the H$^+$ form of this material by Rietveld XRD refinement gave the results shown in Table 1.

Example 14

6.21 g of NaOH, (99%), was dissolved in 111.88 g water to create a sodium hydroxide solution. 1.16 g Al(OH)$_3$ (29.32 wt.-% Al) was added to the sodium hydroxide solution to create a first solution. 0.30 g of the layered material (UZM-8) and 37.5 g Ludox AS-40 were added to the first solution. The first solution was vigorously stirred for 1-2 hours. The first solution was cooled to 0° C.-4° C. Separately, 8.18 g 1,4-dibromobutane (99 wt.-%) was mixed with 9.56 g 1-methylpyrrolidine (97 wt.-%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 170° C. for 96 hours with stirring at 100 rpm. The product was isolated by filtration. The product was identified as UZM-39 by XRD. Analytical results showed this material to have the following molar ratios, Si/Al of 12.76, Na/Al of 0.116, N/Al of 0.94, C/N of 6.98.

Example 15

6.21 g of NaOH, (99%), was dissolved in 111.88 g water to create a sodium hydroxide solution. 1.16 g Al(OH)$_3$ (29.32 wt.-% Al) was added to the sodium hydroxide solution to create a first solution. 0.30 g of the layered material (UZM-8) and 37.5 g Ludox AS-40 were added to the first solution. The first solution was vigorously stirred for 1-2 hours. The first solution was cooled to 0° C.-4° C. Separately, 8.18 g 1,4-dibromobutane (99 wt.-%) was mixed with 9.56 g 1-methylpyrrolidine (97 wt.-%) for 1-5 minutes to form a second solution. The second solution was added to the cooled first solution to create the final reaction mixture. The final reaction mixture was vigorously stirred for approximately 5 minutes and transferred to a 300 cc stirred autoclave. The final reaction mixture was digested at 175° C. for 44 hours with stirring at 100 rpm. The product was isolated by filtration. The product was identified as UZM-39 by XRD. Analytical results showed this material to have the following molar ratios, Si/Al of 12.97, Na/Al of 0.20, N/Al of 0.95, C/N of 6.98.

Example 16

5.96 g of NaOH, (97%) and 0.25 g KOH, (86%) were dissolved in 111.88 g water. 1.22 g Al(OH)$_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. The x-ray diffraction pattern is shown in FIG. 3. Analytical results showed this material to have the following molar ratios, Si/Al of 11.69, Na/Al of 0.137, K/Al of 0.024, N/Al of 0.848, C/N of 7.16.

Figure 4:
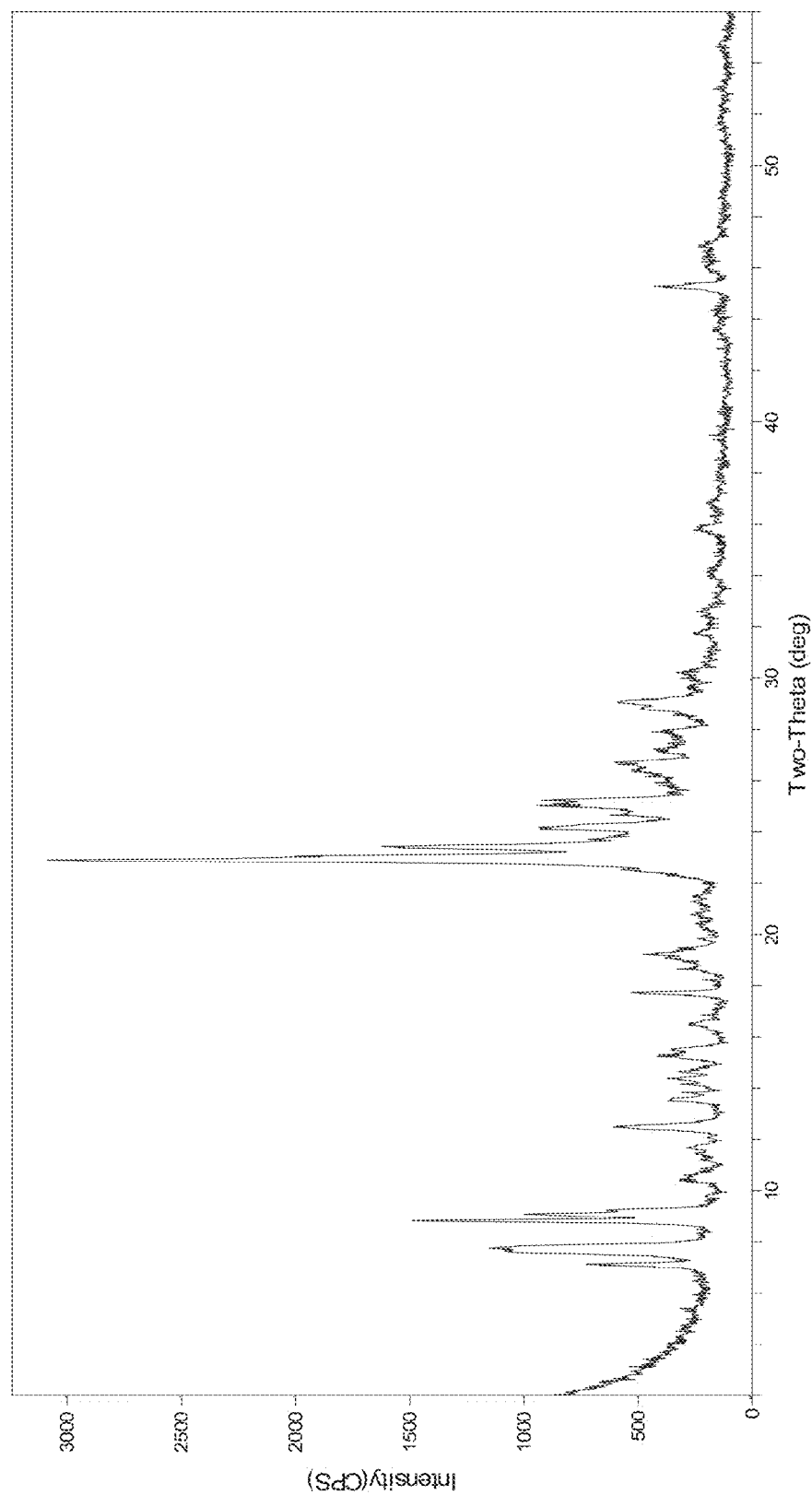
FIG. 4 is also an XRD pattern of the UZM-39 zeolite formed in Example 16. This pattern shows the UZM-39 zeolite in the $H^+$ form.

The product generated by this synthesis was calcined under flowing air at 600° for 6 hours. It was then ion exchanged four times with 1 M ammonium nitrate solution at 75° followed by a calcination at 500° C. under air for 2 hours to convert NH$_4^+$ into H$^+$. Analysis for the calcined, ion-exchanged sample shows 39.4% Si, 3.23% Al, 0.011% Na, 0.005% K with a BET surface area of 362 m$^2$/g, pore volume of 0.231 cm$^3$/g, and micropore volume of 0.176 cm$^3$/g. The x-ray diffraction pattern in shown in FIG. 4.

Example 17

5.96 g of NaOH, (99%) and 0.50 g KOH, (86%) were dissolved in 111.88 g water. 1.16 g Al(OH)$_3$, (29.32 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 4.09 g 1,4-dibromobutane, (99%) was mixed with 11.15 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 11.98, Na/Al of 0.114, K/Al of 0.0375 N/Al of 0.84, C/N of 7.50.

Figure 11:
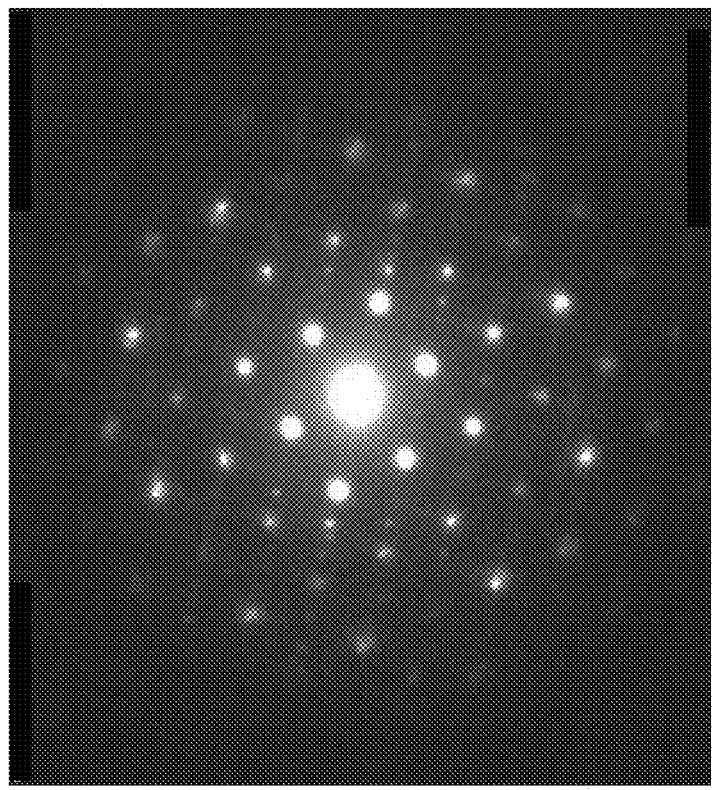
FIG. 11 is an electron diffraction analysis of the cross sectioned rod particle of FIG. 10 and shows that from what appears to be a single-crystalline zeolite particle, areas that index to [010] zone axis of TUN and to [001] zone axis of IMF are found. The TUN regions and IMF regions are coherently aligned.
Figure 11:
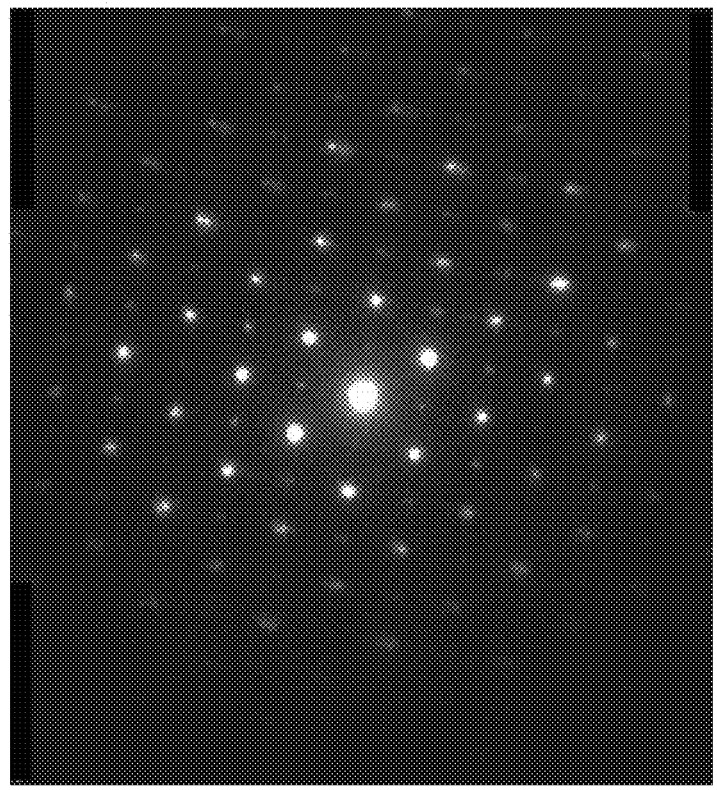

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 37.7% Si, 3.01% Al, 0.012% Na, 0.006% K. Analysis of the $H^+$ form of this material by Rietveld XRD refinement gave the results shown in Table 1. TEM analysis showed that UZM-39 is a coherently grown composite structure of TUN and IMF zeotypes, the results of which analysis are shown in FIGS. 10 and 11.

Example 18

Figure 8:
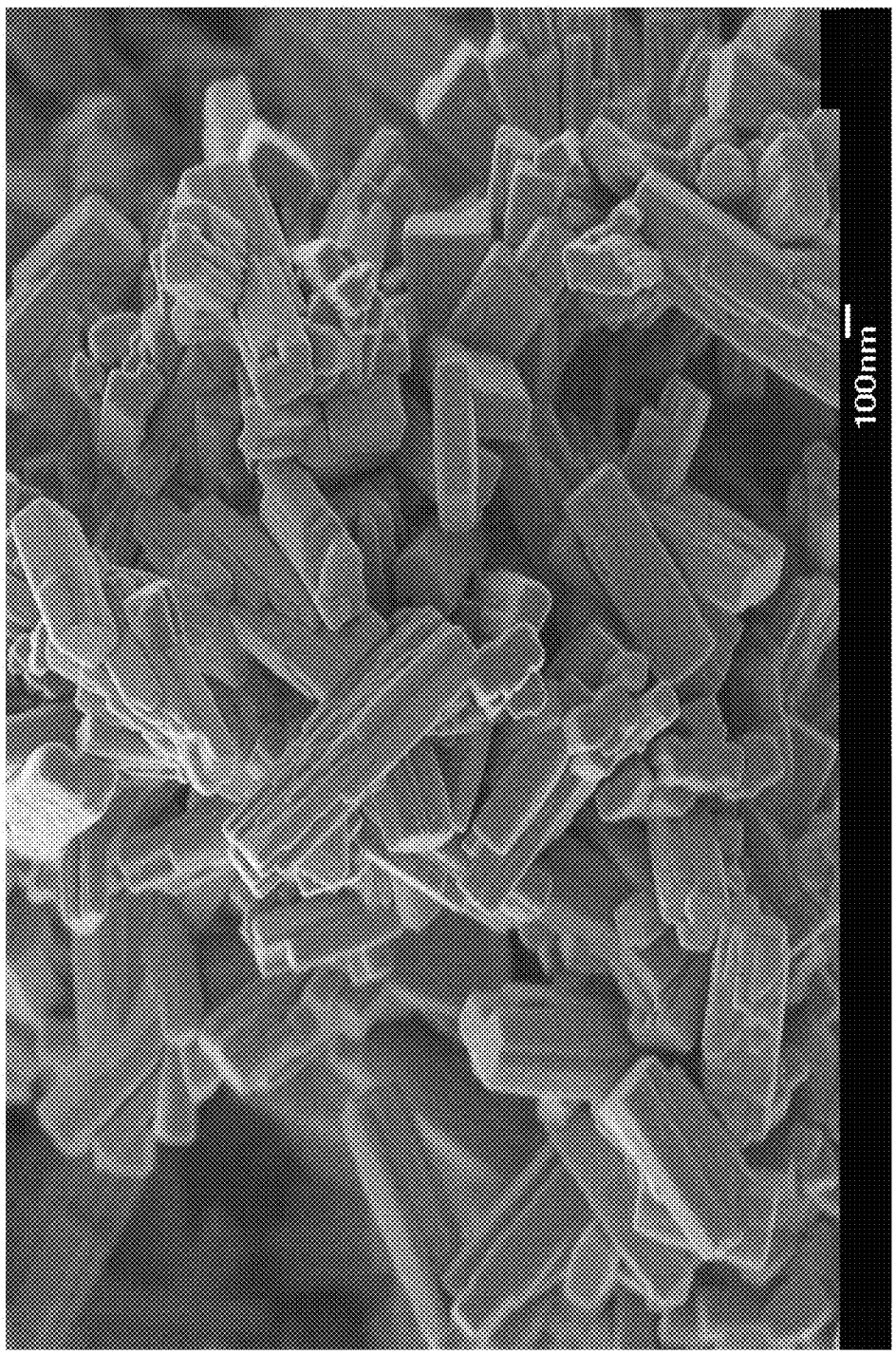
FIG. 8 shows the results of high-resolution scanning electron microscopy characterization of a different UZM-39, that of the product of Example 18. The electron micrograph also shows lathes assembled into rectangular rod particles with a number of starburst cluster arrangements.

5.64 g of NaOH, (97%) and 1.00 g KOH, (86%) were dissolved in 111.88 g water. 1.22 g Al(OH)$_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 11.29, Na/Al of 0.078, K/Al of 0.053 N/Al of 0.88, C/N of 6.92. The SEM image of the product is shown in FIG. 8.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 42.6% Si, 3.65% Al, 0.0018% Na, 0.02% K with a BET surface area of 351 m$^2$/g, pore volume of 0.218 cm$^3$/g, and micropore volume of 0.170 cm$^3$/g. Analysis of the $H^+$ form of this material by Rietveld XRD refinement gave the results shown in Table 1.

Example 19

5.02 g of NaOH, (97%) and 2.00 g KOH, (86%) were dissolved in 111.88 g water. 1.22 g Al(OH)$_3$, (27.9 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 136 hours with stirring at 100 rpm. The product was isolated by filtration. The product was identified as UZM-39 by XRD with a likely small amount of NES contaminant. Analytical results showed this material to have the following molar ratios, Si/Al of 10.99, Na/Al of 0.088, K/Al of 0.11 N/Al of 0.84, C/N of 7.36.

Example 20

5.96 g of NaOH, (99%) was dissolved in 111.88 g water. 1.22 g Al(OH)$_3$, (27.9 wt.-% Al), was added to the sodium hydroxide solution. Then 0.24 g Mg(OH)$_2$ (95%), 37.5 g Ludox AS-40, and 0.30 g of the layered material UZM-8 were added in the order listed to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) and added to the cooled mixture to create the final reaction mixture. The final reaction mixture was vigorously stirred and transferred to a 300 cc stirred autoclave. The final reaction mixture was digested at 160° C. for 144 hours with stirring at 100 rpm. The product was isolated by filtration. The product was identified as UZM-39 by XRD. Analytical results showed this material to have the following molar ratios, Si/Al of 12.12, Na/Al of 0.148, Mg/Al of 0.38 N/Al of 0.91, C/N of 6.96.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 39.6% Si, 2.99% Al, 83 ppm Na, 0.14% Mg with a BET surface area of 351 m$^2$/g, pore volume of 0.218 cm$^3$/g, and micropore volume of 0.170 cm$^3$/g.

Example 21

5.96 g of NaOH, (99%) and 0.51 g La(OH)$_3$, (99.9%) were dissolved in 111.88 g water. 1.16 g Al(OH)$_3$, (29.32 wt.-% Al), was added to the sodium hydroxide solution. 37.5 g Ludox AS-40 and then 0.30 g of the layered material UZM-8 were added to the first solution and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) and added to the cooled mixture to create the final reaction mixture. The final reaction mixture was vigorously stirred and transferred to a 300 cc stirred autoclave. The final reaction mixture was digested at 160° C. for 168 hours with stirring at 100 rpm. The product was isolated by filtration. The product was identified as UZM-39 by XRD. Analytical results showed this material to have the following molar ratios, Si/Al of 12.22, Na/Al of 0.20, La/Al of 0.18, N/Al of 0.89, C/N of 7.13.

The product generated by this synthesis was calcined under flowing air at 600° for 6 hours. It was then ion exchanged four times with 1 M ammonium nitrate solution at 75° followed by a calcination at 500° C. under air for 2 hours to convert $NH_4^+$ into $H^+$. Analysis for the calcined, ion-exchanged sample shows 39.1% Si, 3.06% Al, 60 ppm Na, 0.25% La with a BET surface area of 335 m$^2$/g, pore volume of 0.226 cm$^3$/g, and micropore volume of 0.163 cm$^3$/g.

Example 22

3.14 g of NaOH, (97%) was dissolved in 106.41 g water. 1.16 g Al(OH)$_3$, (29.32 wt.-% Al), was added to the sodium hydroxide solution. 37.5 g Ludox AS-40 and then 0.30 g of the layered material UZM-8 were added to the first solution. Next 26.7 g Na silicate solution (13.2 wt. % Si; 6.76 wt. % Na) is added to the above and stirred vigorously for 1-2 hours. The mixture was cooled to 0° C.-4° C. Separately, 8.18 g 1,4-dibromobutane, (99%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 224 hours with stirring at 100 rpm. The product was isolated by filtration. The product was identified as UZM-39 by XRD. Analytical results showed this material to have the following molar ratios, Si/Al of 11.75, Na/Al of 0.11, N/Al of 0.90, C/N of 6.99.

The product generated by this synthesis was calcined under flowing air at 600° for 6 hours. It was then ion exchanged three times with 1 M ammonium nitrate solution at 75° followed by a calcination at 500° C. under air for 2 hours to convert $NH_4^+$ into $H^+$. Analysis for the calcined, ion-exchanged sample shows 38.8% Si, 3.05% Al, 0.011% Na, with a BET surface area of 364 $m^2/g$, pore volume of 0.273 $cm^3/g$, and micropore volume of 0.174 $cm^3/g$. Analysis of the $H^+$ form of this material by Rietveld XRD refinement gave the results shown in Table 1.

Example 23

5.33 g of NaOH, (99%) was dissolved in 111.88 g water. 1.16 g $Al(OH)_3$, (29.32 wt.-% Al), was added to the sodium hydroxide solution. Separately, 0.30 g of Beta zeolite was stirred into 37.5 g Ludox AS-40 to make a second mixture. This second mixture was added to the first solution and stirred vigorously for 1-2 hours. The mixture was cooled to 0° C.-4° C. Separately, 8.89 g 1,5-dibromopentane, (97%) was mixed with 9.56 g 1-methylpyrrolidine, (97%) to form a third mixture. The third mixture was added to the cooled mixture to create the final reaction mixture. The final reaction mixture was vigorously stirred and transferred to a 300 cc stirred autoclave. The final reaction mixture was digested at 160° C. for 256 hours with stirring at 100 rpm. The product was isolated by filtration. The product was identified as UZM-39 by XRD. Analytical results showed this material to have the following molar ratios, Si/Al of 13.24, Na/Al of 0.13, N/Al of 0.91, C/N of 7.21.

The product generated by this synthesis was calcined under flowing air at 600° for 6 hours. It was then ion exchanged three times with 1 M ammonium nitrate solution at 75° followed by a calcination at 500° C. under air for 2 hours to convert $NH_4^+$ into $H^+$. Analysis of the $H^+$ form of this material by Rietveld XRD refinement gave the results shown in Table 1.

Comparative Example 24

10.8 g of Aerosil 200 was added, while stirring, to a solution of 12.24 g 1,5-bis(N-methylpyrrolidinium)pentane dibromide in 114 g $H_2O$. A very thick gel was formed. Separately, a solution was made from 60 g $H_2O$, 3.69 g NaOH (99%), 0.95 g sodium aluminate (26.1% Al by analysis), and 1.86 g NaBr (99%). This second solution was added to the above mixture which thins out a bit. The final mixture was divided equally between 745 cc Parr vessels. One vessel, which was digested for 12 days at 170° C. in a rotisserie oven at 15 rpm, yielded a product which was determined by XRD as having the IMF structure. The product was isolated by filtration. The product generated by this synthesis was calcined under flowing air at 600° for 6 hours. It was then ion exchanged four times with 1 M ammonium nitrate solution at 75° followed by a calcination at 500° under air for 2 hours to convert $NH_4^+$ into $H^+$. Analysis of the H+-form of this material by Rietveld XRD refinement showed that the material consisted entirely of IMF structure type. TEM analysis confirmed that no coherent growth of TUN crystals occurred.

Example 25

31.98 g of NaOH, (99%) was dissolved in 671.3 g water. 6.96 g $Al(OH)_3$, (29.32 wt.-% Al), was added to the sodium hydroxide solution. Separately, 1.80 g of the layered material UZM-8 was stirred into 225.0 g Ludox AS-40 to make a second mixture. This second mixture was added to the first solution and stirred vigorously for 1-2 hours. The mixture was cooled to 0° C.-4° C. Separately, 53.34 g 1,5-dibromopentane, (97%) was mixed with 57.36 g 1-methylpyrrolidine, (97%) to form a third mixture. The third mixture was added to the cooled mixture to create the final reaction mixture. The final reaction mixture was vigorously stirred and transferred to a 2 L stirred autoclave. The final reaction mixture was digested at 160° C. for 256 hours with stirring at 250 rpm. The product was isolated by filtration. The product was identified as UZM-39 by XRD. Analytical results showed this material to have the following molar ratios, Si/Al of 12.30, Na/Al of 0.13, N/Al of 0.92, C/N of 7.51.

The product generated by this synthesis was calcined under flowing air at 600° for 6 hours. It was then ion exchanged three times with 1 M ammonium nitrate solution at 75° followed by a calcination at 500° under air for 2 hours to convert $NH_4^+$ into $H^+$. Analysis for the calcined, ion-exchanged sample shows 39.0% Si, 2.93% Al, 0.008% Na. Analysis of the H+-form of this material by Rietveld XRD refinement gave the results shown in Table 1.

Example 26

5.76 g of NaOH, (97%) was dissolved in 111.88 g water. 1.22 g $Al(OH)_3$, (27.9 wt.-% Al), was added to the sodium hydroxide solution. When this became a solution, 37.5 g Ludox AS-40 was added. Next 0.30 g of the layered material UZM-8 was added. The mixture was stirred vigorously for 1-2 hours. The mixture was cooled to 0° C.-4° C. Separately, 0.89 g 1,5-dibromopentane, (97%) was mixed with 7.36 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD. Analytical results showed this material to have the following molar ratios, Si/Al of 12.15, Na/Al of 0.15, N/Al of 0.90, C/N of 7.59.

The product generated by this synthesis was calcined under flowing air at 600° C. for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.6% Si, 2.85% Al, <0.01% Na. Analysis of the $H^+$ form of this material by Rietveld XRD refinement gave the results shown in Table 1.

Example 27

5.76 g of NaOH, (97%) was dissolved in 111.88 g water. 1.22 g $Al(OH)_3$, (27.9 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 1.78 g 1,5-dibromopentane, (97%) was mixed with 6.54 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD. Analytical results showed this material to have the following molar ratios, Si/Al of 12.24, Na/Al of 0.107, N/Al of 0.93, C/N of 6.91.

The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.7% Si, 2.98% Al, 158 ppm Na with a BET surface area of 333 m$^2$/g, pore volume of 0.201 cm$^3$/g, and micropore volume of 0.164 cm$^3$/g. Analysis of the $H^+$ form of this material by Rietveld XRD refinement gave the results shown in Table 1.

Example 28

5.76 g of NaOH, (97%) was dissolved in 111.88 g water. 1.22 g Al(OH)$_3$, (27.9 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 2.67 g 1,5-dibromopentane, (97%) was mixed with 5.73 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 176 hours with stirring at 100 rpm. The product was isolated by filtration. The product was identified as UZM-39 by XRD. The x-ray diffraction pattern is shown in FIG. 5. Analytical results showed this material to have the following molar ratios, Si/Al of 12.15, Na/Al of 0.108, N/Al of 0.86, C/N of 7.68.

Figure 6:
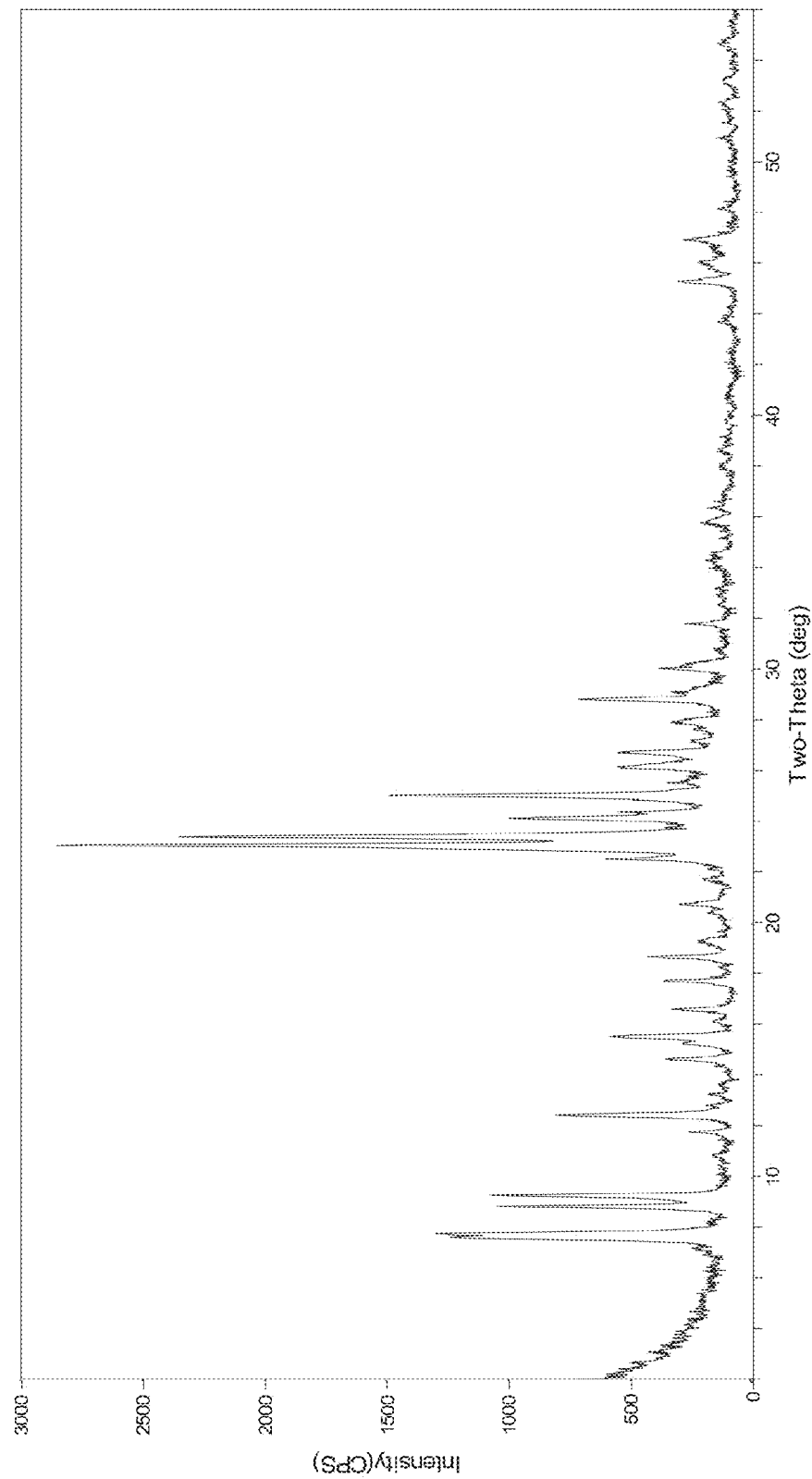
FIG. 6 is also an XRD pattern of the UZM-39 zeolite formed in Example 28. This pattern shows the UZM-39 zeolite in the $H^+$ form.

The product generated by this synthesis was calcined under flowing air at 600° C. for 6 hours. It was then ion exchanged four times with 1 M ammonium nitrate solution at 75° C. followed by a calcination at 500° under air for 2 hours to convert $NH_4^+$ into $H^+$. Analysis for the calcined, ion-exchanged sample shows 38.7% Si, 2.98% Al, 79 ppm Na. The x-ray diffraction pattern is shown in FIG. 6. Analysis of the $H^+$ form of this material by Rietveld XRD refinement gave the results shown in Table 1.

Example 29

5.80 g of NaOH, (97%) was dissolved in 111.88 g water. 1.16 g Al(OH)$_3$, (29.32 wt.-% Al), was added to the sodium hydroxide solution. When this became a solution, 37.5 g Ludox AS-40 was added. Next, 0.30 g of the layered material UZM-8 was added and the mixture was stirred vigorously for 1-2 hours. The mixture was cooled to 0° C.-4° C. Separately, 4.45 g 1,5-dibromopentane, (97%) was mixed with 4.09 g 1,4-dibromobutane, (99%), then 9.56 g 1-methylpyrrolidine, (97%) was added to form a second mixture. The second mixture was added to the cooled mixture to create the final reaction mixture. The final reaction mixture was vigorously stirred and transferred to a 300 cc stirred autoclave. The final reaction mixture was digested at 160° C. for 224 hours with stirring at 100 rpm. The product was isolated by filtration. The product was identified as UZM-39 by XRD. Analytical results showed this material to have the following molar ratios, Si/Al of 11.75, Na/Al of 0.13, N/Al of 0.86, C/N of 7.59.

The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 40.1% Si, 3.32% Al, 90 ppm Na with a BET surface area of 305 m$^2$/g, pore volume of 0.224 cm$^3$/g, and micropore volume of 0.146 cm$^3$/g. Analysis of the $H^+$ form of this material by Rietveld XRD refinement gave the results shown in Table 1.

TABLE 1

| Example # | % TUN | % IMF |
|---|---|---|
| 3 | 100 | 0 |
| 6 | 95 | 5 |
| 13 | 83 | 17 |
| 17 | 46 | 54 |
| 18 | 36.5 | 63.5 |
| 23 | 24 | 76 |
| 24 | 0 | 100 |
| 25 | 19 | 81 |
| 26 | 58 | 42 |
| 27 | 30 | 70 |
| 28 | 13 | 87 |
| 29 | 8 | 92 |

Example 30

To determine the quantities of TUN or IMF structure able to be detected in a UZM-39 coherently grown composite structure material, a detection limit study was performed. A series of simulated diffraction patterns were electronically created from the observed diffraction patterns of the $H^+$ forms of Example 3 and Example 24 products using JADE XRD analysis software (available from Materials Data Incorporated). Mixture levels ranged from 1% to 99% TUN and were created by scaling the smaller percentage constituent to the required level, adding the patterns and saving the composite pattern.

Figure 12:
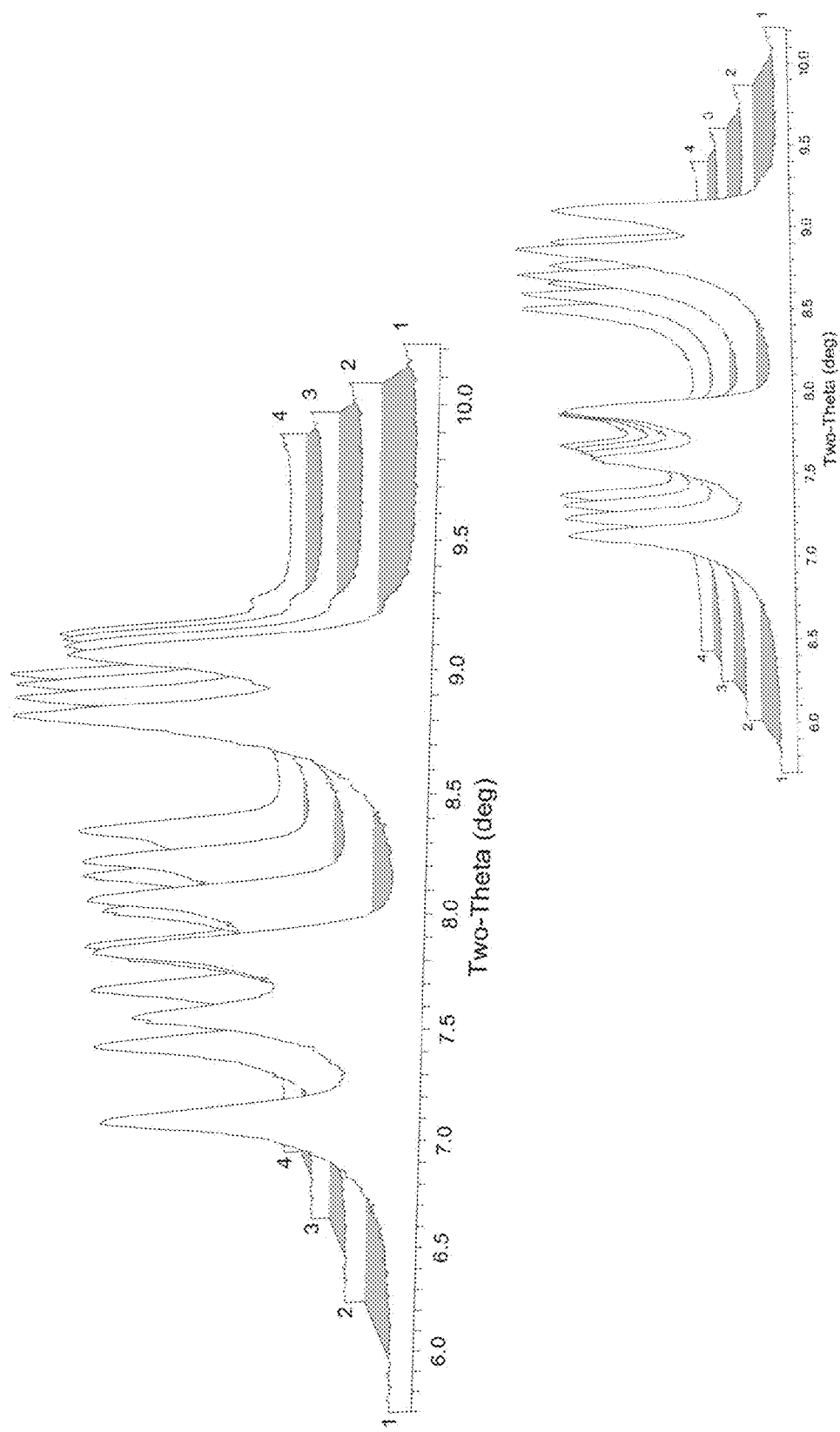
FIG. 12 is a plot of the low angle region in XRD analysis of materials showing that small percentages of IMF can be determined in samples largely consisting of TUN.

Rietveld analysis was able to quantify the level of IMF in the UZM-39 coherently grown composite structure at the 10% or greater level, however visually, small percentages of IMF can be determined in samples (FIG. 12) largely consisting of TUN at the 5% or greater level from intensity of peak at d-spacing of ~9.46 A, while at higher levels, other peaks can be followed such as the increase in peak at d-spacing of ~11.4 A amongst others. In FIG. 12, spectrum 1 is 1% IMF, 99% TUN; spectrum 2 is ~3% IMF, 97% TUN; spectrum 3 is ~5% IMF, 95% TUN; and spectrum 4 is ~10% IMF, 90% TUN.

Rietveld analysis was able to quantify the level of TUN in the UZM-39 coherently grown composite structure at the 10% or greater level, however FIG. 13 shows that, visually, small percentages of TUN can be seen in samples largely consisting of IMF at the 5% or greater level from intensity of peak at d-spacing ~12.25 A, while at higher levels, other peaks can be followed such as the increase in peak at d-spacing of ~9.63 A amongst others. In FIG. 13, spectrum 1 is ~1% TUN, 99% IMF; spectrum 2 is ~3% TUN, 97% IMF; spectrum 3 is ~5% TUN, 95% IMF; and spectrum 4 is ~10% TUN, 90% IMF.

Example 31

44.9 g of NaOH, (97%) was dissolved in 1122.3 g water. To this solution was added 10.8 g liquid sodium aluminate (22.9% Al₂O₃, 20.2% Na₂O) followed by 105.9 g Ultrasil VN3 (90% SiO₂, available from Evonik) to form a first mixture. Separately, 53.5 g 1,4-dibromobutane, (99%), was combined with 62.6 g 1-methylpyrrolidine, (97%) to form a second mixture. The second mixture was added to the first mixture to create the final reaction mixture. Last, 1 g of the layered material UZM-8 was added and the mixture was stirred vigorously for 1-2 hours before transferring to a 2 L stirred autoclave. The final reaction mixture was digested at 160° C. for 7 days while stirring at 200 rpm. The product was isolated by filtration and identified as UZM-39 by XRD. Analytical results showed this material to have the following molar ratios, Si/Al of 12.40, Na/Al of 0.21, N/Al of 1.10, C/N of 7.06.

Example 32

NaOH, Al(OH)₃, Ga(NO3)3.9H₂O, Ludox AS-40, 1,4-dibromobutane, 1-methylpyrrolidine, water and layered material UZM-8 were combined to form a mixture of composition 0.5 Al₂O₃:0.5 Ga₂O₃:65.4 SiO₂:24.6 Na₂O:9.9 C₄Br₂:29.41-MP:2636 H₂O and stirred vigorously for 1-2 hours before transferring to a 2 L stirred autoclave. The final reaction mixture was digested at 160° C. for 150 hours while stirring at 250 rpm. The product was isolated by filtration and identified as UZM-39 by XRD. Analytical results showed this material to have the following molar ratios, Si/Al of 21.61, Si/Ga of 31.35, Si/(Al+Ga) of 12.79, Na/(Al+Ga) of 0.10, N/(Al+Ga) of 0.91, C/N of 7.39.

Example 33

A UZM-39 containing a high quantity of TUN and low quantity of IMF in the H+ form was loaded into a vertical steamer. The UZM-39 was exposed to 100% steam at 725° C. for 12 hours or 24 hours. The starting UZM-39 had a BET surface area of 385 m²/g, pore volume of 0.248 cm³/g, and micropore volume of 0.180 cm³/g. After 12 hours of steaming, the UZM-39 was still identified as UZM-39 by XRD though the intensity of the first 5 peaks had increased to strong, strong, very strong, strong and medium respectively. All other peaks were at positions and intensities described in Table B. The material had a BET surface area of 331 m²/g, pore volume of 0.243 cm³/g, and micropore volume of 0.151 cm³/g. After 24 hours of steaming, the UZM-39 was still identified as UZM-39 by XRD though the intensity of the first 5 peaks had increased to medium-strong, strong, strong, medium-strong and medium respectively. All other peaks were at positions and intensities described in Table B. The material had a BET surface area of 327 m²/g, pore volume of 0.241 cm³/g, and micropore volume of 0.150 cm³/g.

Example 34

A UZM-39 containing a high quantity of TUN and low quantity of IMF in the H+ form was put into a round bottom flask containing 6N HNO₃ and outfitted with a condenser and stirrer. The mixture containing UZM-39 and HNO₃ was boiled at reflux for 8 or 16 h. The resulting material was filtered, washed and dried. XRD analysis showed the material to be UZM-39 consistent with Table B.

Example 35

The H+ form of UZM-39 with a high TUN content was impregnated with about 4 wt.-% of molybdenum and then calcined in air at 500° C. for about 3 hours, and labeled Catalyst UZM-39H-Mo. To simulate high temperature deactivation, the catalyst was then subjected to calcination in air at 750° C. for 60 hours. The activity of 1 gram of catalyst UZM-39H-Mo with and without the high temperature deactivation was tested by contacting a feedstream containing 90% wt.-% methane, 5 wt.-% hydrogen, and 5 wt.-% argon at 750° C. and 1600 hr⁻¹ GHSV on methane and 2 psig for a run time of 3.5 hours and then measuring the aromatics yield. As a comparison, the experiment was repeated for a 3.5 hour run time using the H+ form of an MFI catalyst impregnated with 4 wt.-% molybdenum (labeled Catalyst MFI-H-Mo), both with and without the simulated high temperature deactivation of calcination in air at 750° C. for about 60 hours. Table 2 shows the total aromatics yield in wt.-% of each catalyst averaged over a 3.5 hour run time, both with and without the simulated deactivation. The results show that after the simulated deactivation catalyst UZM-39H-Mo demonstrated higher yield for total aromatics than that achieved using catalyst MFI-H-Mo. Thus the catalyst of the invention deactivated to a lesser extent.

The above comparison was repeated using tungsten as the impregnated promoter instead of molybdenum. The H+ form of UZM-39 was impregnated to result in about 8 wt.-% of tungsten and then calcined in air at 500° C. for about 3 hours, and labeled Catalyst UZM-39H-W. To simulate high temperature deactivation, the catalyst was then subjected to calcination in air at 750° C. for 60 hours. The activity of 1 gram of catalyst UZM-39H-W with and without the high temperature deactivation was tested by contacting a feedstream containing 90% wt-% methane, 5 wt.-% hydrogen, and 5 wt.-% argon at 750° C. and 1600 hr–1 GHSV and 2 psig on methane for a run time of 3.5 hours and then measuring the aromatics yield. As a comparison, the experiment was repeated for a 3.5 hour run time using 1 gram of the H+ form of an MFI catalyst impregnated with 8 wt.-% tungsten (labeled Catalyst MFI-H-W), both with and without the simulated high temperature deactivation of calcination in air at 750° C. for about 60 hours. Table 2 shown the total aromatics yield in wt.-% of each catalyst averaged over a 3.5 hour run time, both with and without the simulated deactivation. The results show that after the simulated deactivation catalyst UZM-39H-W demonstrated higher yield for total aromatics than that achieved using catalyst MFI-H-W or MFI-H-Mo. In addition, the UZM-39 catalyst composites had higher amounts of Brønsted acid sites and lower ratios of Al₂(MoO₄)₃/Al(4) and Al(6)/Al (4) after the simulated deactivation than did MFI catalyst composites, see Table 3. Thus the catalyst of the invention deactivated to a lesser extent. The results shown in Table 2 were generated using a first set of starting materials for the zeolites tested and the results shown in Table 3 were generated using a second set of starting materials for the zeolites. In addition, the catalysts of Table 3 were calcined for only about 3 hours at the temperature indicated.

TABLE 2

| Catalyst | Average Total Aromatics Yield, wt-% | |
|---|---|---|
| | Without Simulated Deactivation | After Simulated Deactivation |
| UZM-39H-Mo | 3.3 | 2.5 |
| MFI-H-Mo | 3.3 | 0.4 |
| UZM-39H-W | 1.8 | 1.5 |
| MFI-H-W | 2.0 | 0.6 |

TABLE 3

| Catalyst | Al27 NMR | | | | # of Broensted acid sites by Py-FTIR | Av total aromatics yield 4 hrs test @ 750° C., 1600 GHSV |
|---|---|---|---|---|---|---|
| | Al2(MoO4)3 | Al(4) | Al(6) | Total integr.intensity | | |
| parent H-MFI | 0 | 93.5 | 6.5 | n/a | 0.418 | |
| 4% Mo/MFI, calc. 500° C. | 3.5 | 45.8 | 4.7 | 54 | 0.297 | 5.16 |
| above, calc.750° C. 3 h | 17.7 | 16.5 | 8.8 | 43 | 0.037 | 2.72 |
| 1.5% Mo/MFI, calc.500° C. | | | | | | 3.88 |
| above, calc.750° C. 3 h | | | | | | 2.92 |
| H-UZM-39 | 0 | 83 | 17 | 100 | 0.401 | |
| 4% Mo/UZM-39, calc.500° C. | 0 | 81 | 19 | 100 | 0.324 | 4.52 |
| above, calc.750° C. 3 h | weak | 61 | 39 | 92 | 0.134 | 3.54 |
| H-UZM-39 | 0 | 85 | 15 | 100 | 0.389 | |
| 1.5% Mo/UZM-39, calc.500° C. | 0 | 82 | 18 | 96 | 0.383 | 2.23 |
| above, calc.750° C. 3 h | weak | 69 | 31 | 76 | 0.159 | 3.20 |

The invention claimed is:

1. A process for converting at least one low carbon number aliphatic hydrocarbon in a feedstream to provide at least one aromatic hydrocarbon, the process comprising contacting the feedstream at reaction conditions with a catalyst to generate at least one aromatic hydrocarbon, the catalyst comprising a coherently grown composite of TUN and IMF zeotypes having a three-dimensional framework of at least $AlO_2$ and $SiO_2$ tetrahedral units and an empirical composition in the as synthesized and anhydrous basis expressed by an empirical formula of:

$$Na_n M_m^{k+} T_t Al_{1-x} E_x Si_y O_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having from 3 to 6 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k\cdot m+3+4\cdot y)/2$$

and is characterized by a characteristic selected from the group consisting of (a) it has TUN regions and IMF regions that are coherently aligned so that the $[010]_{TUN}$ zone axis and the $[001]_{IMF}$ zone axis are parallel to each other and there is continuity of crystal planes of type $(002)_{TUN}$ and $(060)_{IMF}$, where the indexing is referred to monoclinic $C_{2/m}$ and orthorhombic $C_{mcm}$ unit cells for TUN and IMF respectively, (b) it has the x-ray diffraction pattern having at least the d-spacings and intensities set forth in Table A1:

TABLE A1

| 2θ | d (Å) | I/Io % |
|---|---|---|
| 7.17-7.21 | 12.25-12.31 | vw-m |
| 7.5-8.1* | 11.78-10.91 | w-m |
| 8.88 | 9.95 | m |
| 9.17 | 9.63 | w-m |
| 12.47-12.62 | 7.09-7.00 | w-m |
| 17.7 | 5.01 | vw-m |
| 22.8-23.2 | 3.90-3.83 | vs |
| 23.39-23.49 | 3.80-3.78 | m-s |
| 25.01-25.31 | 3.56-3.52 | m |
| 28.74-29.25 | 3.10-3.05 | w-m |
| 45.08-45.29 | 2.01-2.00 | w |

*composite peak consisting of multiple overlapping reflections and (c) combinations thereof.

2. The process of claim 1 wherein the feedstream comprises methane.

3. The process of claim 1 wherein the contacting is in the presence of CO, $CO_2$ and combinations thereof.

4. The process of claim 3 wherein the contacting is in the presence of CO, CO2 or mixtures thereof in a carbon oxides to methane mole ratio of about 0.01 to about 0.3.

5. The process of claim 1 wherein the aromatic hydrocarbon is benzene.

6. The process of claim 1 wherein the catalyst further comprises a promoter selected from the group consisting of iron, cobalt, vanadium, manganese, gallium, zinc, chromium, tungsten, molybdenum and combinations thereof.

7. The process of claim 6 wherein the promoter is present in an amount ranging from about 0.001 to about 25 wt.-% of the catalyst.

8. The process of claim 1 wherein the reaction conditions comprise a temperature from about 300° C. to about 1000° C., a pressure from about 10 kPa to about 1,000 kPa, and a space velocity from about 100 to about 20,000 $hr^{-1}$.

9. The process of claim 1 wherein the coherently grown composite of TUN and IMF zeotypes has a micropore volume as a percentage of total pore volume of greater than 60%.

10. A process for converting at least one aliphatic hydrocarbon having from 1 to about 4 carbon atoms in a feedstream to provide at least one aromatic hydrocarbon, the process comprising contacting the feedstream at reaction conditions with a catalyst to generate at least one aromatic hydrocarbon, the catalyst comprising a coherently grown composite of TUN and IMF zeotypes having a three-dimensional framework of at least $AlO_2$ and $SiO_2$ tetrahedral units and an empirical composition in the hydrogen form after calcination, ion-exchange and calcination and on an anhydrous basis expressed by an empirical formula of $$M1_a^{N+}Al_{(1-x)}E_xSi_{y'}O_{z''}$$

and where M1 is at least one exchangeable cation selected from the group consisting of alkali, alkaline earth metals, rare earth metals, zinc, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, "x" is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

and is characterized by a characteristic selected from the group consisting of (a) it has TUN regions and IMF regions that are coherently aligned so that the $[010]_{TUN}$ zone axis and the $[001]_{IMF}$ zone axis are parallel to each other and there is continuity of crystal planes of type $(002)_{TUN}$ and $(060)_{IMF}$, where the indexing is referred to monoclinic $C_{2/m}$ and orthorhombic $C_{mcm}$ unit cells for TUN and IMF respectively, (b) it has the x-ray diffraction pattern having at least the d-spacings and intensities set forth in Table B1:

TABLE B1

| 2θ | d (Å) | I/Io % |
|---|---|---|
| 7.11-7.16 | 12.42-12.25 | vw-m |
| 7.5-8.1* | 11.78-10.91 | m-s |
| 8.84 | 10.00 | m-s |
| 9.06-9.08 | 9.75-9.73 | w-m |
| 9.24 | 9.56 | vw-m |
| 12.46-12.53 | 7.10-7.06 | w-m |
| 22.56 | 3.94 | vw-m |
| 22.75-23.2 | 3.90-3.83 | vs |
| 23.40 | 3.80 | m-s |
| 24.12-24.23 | 3.69-3.67 | w-m |
| 24.92-25.37 | 3.57-3.51 | m |
| 28.71-29.27 | 3.11-3.05 | w-m |
| 45.32-45.36 | 2.00 | w |

*composite peak consisting of multiple overlapping reflections and (c) combinations thereof.

11. The process of claim 10 wherein the feedstream comprises methane.

12. The process of claim 10 wherein the contacting is in the presence of CO, $CO_2$, or combinations thereof.

13. The process of claim 10 wherein the contacting is in the presence of CO, $CO_2$ or mixtures thereof in a carbon oxides to methane mole ratio of about 0.01 to about 0.3.

14. The process of claim 10 wherein the aromatic hydrocarbon is benzene.

15. The process of claim 10 wherein the catalyst further comprises a promoter selected from the group consisting of iron, cobalt, vanadium, manganese, gallium, zinc, chromium, tungsten, molybdenum and combinations thereof.

16. The process of claim 15 wherein the promoter is present in an amount ranging from about 0.001 to about 25 wt.-% of the catalyst.

17. The process of claim 10 wherein the reaction conditions comprise a temperature from about 300° C. to about 1000° C., a pressure from about 10 kPa to about 1,000 kPa, and a space velocity from about 100 to about 20,000 hr$^{-1}$.

* * * * *